(12) United States Patent
Acemoglu et al.

(10) Patent No.: US 7,989,494 B2
(45) Date of Patent: Aug. 2, 2011

(54) POLYMORPHS OF N-HYDROXY-3-[4-[[[2-(2-METHYL-1H-INDOL-3-YL)ETHYL]AMINO]METHYL]PHENYL]-2E-2-PROPENAMIDE

(75) Inventors: Murat Acemoglu, Basel (CH); Joginder S. Bajwa, Elmwood Park, NJ (US); Piotr Karpinski, Lincoln Park, NJ (US); Dimitris Papoutsakis, Acton, MA (US); Joel Slade, Flanders, NJ (US); Frank Stowasser, Murg (DE)

(73) Assignee: Novartis AG, Basel (CH)

( * ) Notice: Subject to any disclaimer, the term of this patent is extended or adjusted under 35 U.S.C. 154(b) by 224 days.

(21) Appl. No.: 12/302,564

(22) PCT Filed: Jun. 7, 2007

(86) PCT No.: PCT/US2007/070561
§ 371 (c)(1),
(2), (4) Date: Nov. 26, 2008

(87) PCT Pub. No.: WO2007/146716
PCT Pub. Date: Dec. 21, 2007

(65) Prior Publication Data
US 2009/0192210 A1 Jul. 30, 2009

Related U.S. Application Data

(60) Provisional application No. 60/804,517, filed on Jun. 12, 2006, provisional application No. 60/883,224, filed on Jan. 3, 2007.

(51) Int. Cl.
*A61K 31/404* (2006.01)
*C07D 209/10* (2006.01)
*C07D 209/12* (2006.01)
*C07D 209/14* (2006.01)

(52) U.S. Cl. ........................................ 514/503; 548/503

(58) Field of Classification Search ........................ None
See application file for complete search history.

(56) References Cited

U.S. PATENT DOCUMENTS

2009/1297936    8/2009   Acemoglu
2010/0286409 A1 11/2010  Acemoglu

FOREIGN PATENT DOCUMENTS

| WO | WO-02/22577    | 3/2002 |
| WO | WO 03/039599   | 5/2003 |
| WO | WO 03/048774   | 6/2003 |
| WO | WO 2004/103358 | 2/2004 |
| WO | 2005/013958    | 2/2005 |
| WO | 2005/027972    | 3/2010 |

OTHER PUBLICATIONS

Giles, et al., Clin. Cancer Res. 12:4628 (2006).*
Ellis, et al., Clin. Cancer Res., 14:4500 (2008).*
Rathkopf, et al., J. Clin. Oncol. 26:abstr# 5152 (2008).*
Duvic, et al., J. Clin. Oncol., 26:abstr 8555 (2008).*
Tan et al., J. Hematology & Oncology, 3:5 (2010).*
Schafer et al. Drug Discovery Today, 13:913 (2008).*
Horig et al. Journal of Translational Medicine, 2:44 (2004).*
Soghoian Samara et al: "Toxicity, heavy metals", eMedicine from WebMD (15 pages) accessed online Dec. 28, 2009.
Bastin Richard J et al: "Salt selection and optimisation procedures for pharmaceutical new chemical entities", Organic Process Research & Development, 2000, vol. 4, pp. 427-435.
Alfa Aesar catalog, Lactic acid entry, accessed online Dec. 29, 2009.
Chemindustry.com entry for "EINECS No. 200-018-0" accessed online Dec. 20, 2009.
Stacy W. Remiszewski, S.W. et al., "N-Hydroxy-3-phenyl-2-propenamides as Novel Inhibitors of Human Histone Deacetylase with in Vivo Antitumor Activity: Discovery of (2E)-N-Hydroxy-3-[4-[[(2-hydroxyethyl)[2-(1H-indol-3-yl)ethyl]amino]methyl]-phenyl]-2-propenamide (NVP-LAQ824)" Journal of Medicinal Chemistry, US American Chemical Society, Washington, vol. 46, Jan. 1, 2003 pp. 4609-4624.
International Search Report by Austrian Patent Office for Singapore application No. 200808629-0, (Aug. 6, 2010).
U.S. Appl. No. 12/302,571 Office Action dated Oct. 9, 2009.
U.S. Appl. No. 12/302,571 Office Action dated Jan. 7, 2010.
U.S. Appl. No. 12/775,001 Office Action dated Sep. 17, 2010.

* cited by examiner

*Primary Examiner* — Kamal Saeed
*Assistant Examiner* — Michael Barker
(74) *Attorney, Agent, or Firm* — Matthew Mulkeen

(57) ABSTRACT

Polymorphic forms of N-hydroxy-3-[4-[[[2-(2-methyl-1H-indol-3-yl)ethyl]amino]methyl]phenyl]-2E-2-propenamide free base and salts thereof are prepared by various processes.

42 Claims, 17 Drawing Sheets

US 7,989,494 B2

POLYMORPHS OF N-HYDROXY-3-[4-[[[2-(2-METHYL-1H-INDOL-3-YL)ETHYL]AMINO]METHYL]PHENYL]-2E-2-PROPENAMIDE

This application claims benefit of U.S. Provisional Application No. 60/804,517 filed 12 Jun. 2006 and U.S. Provisional Application No. 60/883,224 filed 3 Jan. 2007, which in their entirety are herein incorporated by reference.

BACKGROUND OF THE INVENTION

1. Field of the Invention

This invention relates to crystalline forms or polymorphs of N-hydroxy-3-[4-[[[2-(2-methyl-1H-indol-3-yl)ethyl]amino]methyl]phenyl]-2E-2-propenamide, as well as to methods of making the same, pharmaceutical compositions comprising the same and methods of treatment using the same.

2. Related Background Art

Polymorphism denotes the existence of more than one crystal structure of a substance. This ability of a chemical substance to crystallize in more than one crystal modification can have a profound effect on the physicochemical properties, shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown polymorphic form during manufacture can have an enormous impact.

Understanding and controlling polymorphism, then, gives a decided advantage in bringing new drugs to the marketplace. First and foremost, predicting any possible polymorphs for a drug product can be used to diminish the possibility of contamination during a drug's manufacture or storage by other polymorphic forms. Failure to catch contamination can have life-threatening consequences in some cases. Crystallizing an unintended polymorph during manufacture can mean weeks or even months of production downtime while scientists find and correct the cause of the new crystal form or go through another round of testing to obtain approval for the new form.

Second, understanding which crystal structures are possible in some cases allows researchers to maximize the desired properties of a compound such as solubility, formulation properties, processing properties, and shelf life. Understanding these factors early in the development of a new drug may mean a more active, more stable, or more cheaply manufactured drug.

The compound N-hydroxy-3-[4-[[[2-(2-methyl-1H-indol-3-yl)ethyl]amino]methyl]phenyl]-2E-2-propenamide (alternatively, N-hydroxy-3-(4-{[2-(2-methyl-1H-indol-3-yl)-ethylamino]-methyl}-phenyl)-acrylamide) has the formula (I):

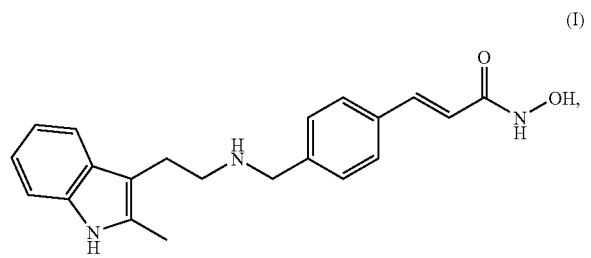

(I)

as described in WO 02/22577. Valuable pharmacological properties are attributed to this compound; thus, it can be used, for example, as a histone deacetylase inhibitor useful in therapy for diseases which respond to inhibition of histone deacetylase activity. Knowledge of the potential polymorphic forms of N-hydroxy-3-[4-[[[2-(2-methyl-1H-indol-3-yl)ethyl]amino]methyl]phenyl]-2E-2-propenamide is useful in the development of a suitable dosage form, because the failure to utilize a single polymorphic form during clinical or stability studies may result in the exact dosage form being used or studied not being comparable from one lot to another. Once chosen, it is important that a polymorphic form can be reproducibly prepared and remain unchanged for prolonged time periods in the dosage form developed. It is also desirable to have a process for producing N-hydroxy-3-[4-[[[2-(2-methyl-1H-indol-3-yl)ethyl]amino]methyl]phenyl]-2E-2-propenamide in high purity since the presence of impurities may produce undesired toxicological effects.

WO 02/22577 provides no information at all about possible crystal modifications of N-hydroxy-3-[4-[[[2-(2-methyl-1H-indol-3-yl)ethyl]amino]methyl]phenyl]-2E-2-propenamide. It has now surprisingly been found that the different crystal modifications (novel polymorphic forms of N-hydroxy-3-[4-[[[2-(2-methyl-1H-indol-3-yl)ethyl]amino]methyl]phenyl]-2E-2-propenamide) characterized below can be prepared by choice of specially selected process conditions, e.g., choice of solvent system, duration of crystallization, etc.

SUMMARY OF THE INVENTION

The present invention is directed to substantially pure crystalline forms of N-hydroxy-3-[4-[[[2-(2-methyl-1H-indol-3-yl)ethyl]amino]methyl]phenyl]-2E-2-propenamide free base and substantially pure crystalline forms of salts of N-hydroxy-3-[4-[[[2-(2-methyl-1H-indol-3-yl)ethyl]amino]methyl]phenyl]-2E-2-propenamide.

The invention is further directed to pharmaceutical compositions comprising:
 (a) a therapeutically effective amount of a substantially pure crystalline form of N-hydroxy-3-[4-[[[2-(2-methyl-1H-indol-3-yl)ethyl]amino]methyl]phenyl]-2E-2-propenamide free base or salt thereof of the present invention; and
 (b) at least one pharmaceutically acceptable carrier, diluent, vehicle or excipient.

The present invention is also directed to a method of treating a disease which responds to an inhibition of histone deacetylase activity comprising the step of administering to a subject in need of such treatment a therapeutically effective amount of a substantially pure crystalline form of N-hydroxy-3-[4-[[[2-(2-methyl-1H-indol-3-yl)ethyl]amino]methyl]phenyl]-2E-2-propenamide free base or salt thereof of the present invention.

DETAILED DESCRIPTION OF THE INVENTION

N-hydroxy-3-[4-[[[2-(2-methyl-1H-indol-3-yl)ethyl]amino]methyl]phenyl]-2E-2-propenamide free base can be obtained in the novel polymorphic forms A, B, C, $H_A$ and $H_B$. These "crystal modifications" (or "polymorphic form(s)", "polymorph(s)" or "crystalline form(s)", as the terms will be used interchangeably herein) differ with respect to their x-ray powder diffraction patterns, physicochemical and pharmacokinetic properties, and thermodynamic stability. For purposes of this invention, various hydrate and solvate forms are included in the scope of "polymorphic forms". The crystalline forms of N-hydroxy-3-[4-[[[2-(2-methyl-1H-indol-3-yl)ethyl]amino]methyl]phenyl]-2E-2-propenamide free base to which the present invention is directed are characterized by the x-ray powder diffraction patterns (XRPD) shown in FIG. 1.

As used herein, the terms "isolated" and/or "substantially pure" mean more than 50% of the crystalline N-hydroxy-3-[4-[[[2-(2-methyl-1H-indol-3-yl)ethyl]amino]methyl]phenyl]-2E-2-propenamide or salt thereof is present in one of the forms described herein and preferably at least 70%, more preferably at least 80%, and most preferably at least 90% of one of the crystalline forms described herein is present.

Figure 1:
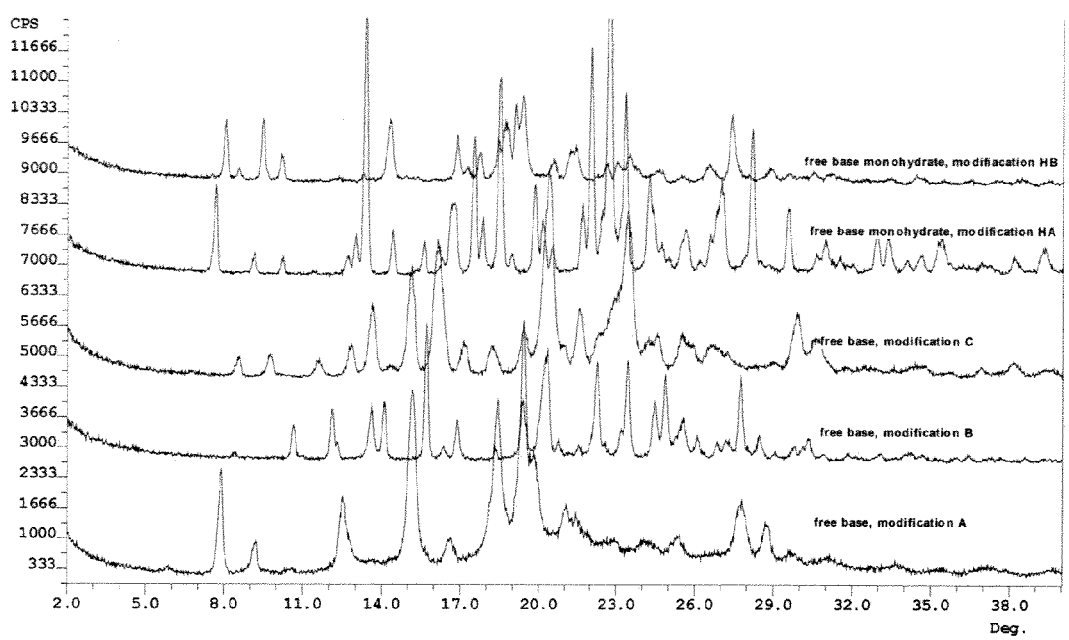
FIG. 1 shows the x-ray powder diffraction patterns for forms A, B, C, $H_A$ and $H_B$ of N-hydroxy-3-[4-[[[2-(2-methyl-1H-indol-3-yl)ethyl]amino]methyl]phenyl]-2E-2-propenamide free base according to the present invention.

The first embodiment of the present invention is directed to a substantially pure polymorphic form A of N-hydroxy-3-[4-[[[2-(2-methyl-1H-indol-3-yl)ethyl]amino]methyl]phenyl]-2E-2-propenamide free base. The x-ray powder diffraction pattern thereof shows at least two, more preferably at least four, and most preferably all, maxima selected from 7.9, 9.2, 12.5, 15.2, 18.4, 19.4, 19.7, 19.8, 27.7 and 28.7 (2θ degrees). A particularly preferred embodiment is directed to a substantially pure polymorphic form A of N-hydroxy-3-[4-[[[2-(2-methyl-1H-indol-3-yl)ethyl]amino]methyl]phenyl]-2E-2-propenamide free base as shown in FIG. 1. Anhydrous form A can be isolated directly from ethanol-water solutions with low water content (EtOH:$H_2O$=20:1). Intermediate water content (EtOH:$H_2O$=10:1 and 7.5:1) produces mixtures of form A and form $H_B$ (the monohydrate of form A). Form A is soluble in hot ethanol, has a broad melting with the onset around 110° C. followed by decomposition at around 130° C. Loss on drying (LOD) is less than 0.7% at 110° C.

The second embodiment of the present invention is directed to a substantially pure polymorphic form B of N-hydroxy-3-[4-[[[2-(2-methyl-1H-indol-3-yl)ethyl]amino]methyl]phenyl]-2E-2-propenamide free base. The x-ray powder diffraction pattern thereof shows at least two, more preferably at least four, and most preferably all, maxima selected from 10.6, 12.1, 13.6, 14.1, 15.7, 16.9, 19.4, 20.3, 22.2, 23.4, 24.4, 24.8, 25.5 and 27.7 (2θ degrees). A particularly preferred embodiment is directed to a substantially pure polymorphic form B of N-hydroxy-3-[4-[[[2-(2-methyl-1H-indol-3-yl)ethyl]amino]methyl]phenyl]-2E-2-propenamide free base as shown in FIG. 1. Anhydrous form B is insoluble in hot ethanol; upon heating, it decomposes without melting at around 187° C. LOD is less than 0.15% at 160° C.

The third embodiment of the present invention is directed to a substantially pure polymorphic form C of N-hydroxy-3-[4-[[[2-(2-methyl-1H-indol-3-yl)ethyl]amino]methyl]phenyl]-2E-2-propenamide free base. The x-ray powder diffraction pattern thereof shows at least two, more preferably at least four, and most preferably all, maxima selected from 8.5, 9.7, 11.6, 12.8, 13.6, 15.1, 16.1, 17.1, 18.2, 19.4, 20.4, 21.5, 22.9, 23.4, 24.5, 25.5, 29.9 and 30.5 (2θ degrees). A particularly preferred embodiment is directed to a substantially pure polymorphic form C of N-hydroxy-3-[4-[[[2-(2-methyl-1H-indol-3-yl)ethyl]amino]methyl]phenyl]-2E-2-propenamide free base as shown in FIG. 1. Form $H_A$ can be completely dehydrated to convert to anhydrous form C, which can rehydrate back to form $H_A$ upon storage at ambient conditions. Anhydrous form C is soluble in hot ethanol-water mixture; upon heating, it melts with decomposition at around 149° C. LOD is less than 0.9% at 140° C.

The fourth embodiment of the present invention is directed to a substantially pure polymorphic form $H_A$ of N-hydroxy-3-[4-[[[2-(2-methyl-1H-indol-3-yl)ethyl]amino]methyl]phenyl]-2E-2-propenamide free base. The x-ray powder diffraction pattern thereof shows at least two, more preferably at least four, and most preferably all, maxima selected from 7.7, 13.0, 13.4, 14.4, 16.7, 17.5, 17.8, 18.5, 19.8, 20.1, 21.7, 22.0, 22.3, 22.7, 23.3, 24.2, 24.4, 25.6, 27.0, 28.1 and 29.5 (2θ degrees). A particularly preferred embodiment is directed to a substantially pure polymorphic form $H_A$ of N-hydroxy-3-[4-[[[2-(2-methyl-1H-indol-3-yl)ethyl]amino]methyl]phenyl]-

2E-2-propenamide free base as shown in FIG. 1. Form $H_A$ is the monohydrate of form C. Higher water (EtOH:H$_2$O=5:1 or 3:1) produces form $H_A$. Form $H_A$ completely dehydrates and converts to form C under vacuum even at ambient temperature. Form C will spontaneously rehydrate to form $H_A$ upon storage at ambient conditions. Form $H_A$ has a relatively high decomposition temperature of 150° C. It is slightly hygroscopic, has poor solubility in water, approximately 0.004 mg/mL, and better solubility in common organic solvents (approx. 1.5 mg/mL in ethanol, approx. 2.3 mg/mL in methanol, approx. 5.6 mg/mL in ethyl acetate). LOD of 4.8% corresponds to monohydrate.

The fifth embodiment of the present invention is directed to a substantially pure polymorphic form $H_B$ of N-hydroxy-3-[4-[[[2-(2-methyl-1H-indol-3-yl)ethyl]amino]methyl]phenyl]-2E-2-propenamide free base. The x-ray powder diffraction pattern thereof shows at least two, more preferably at least four, and most preferably all, maxima selected from 8.0, 9.5, 10.2, 14.3, 16.9, 17.7, 18.4, 18.7, 19.1, 19.4, 21.2, 21.4 and 27.4 (2θ degrees). A particularly preferred embodiment is directed to a substantially pure polymorphic form $H_B$ of N-hydroxy-3-[4-[[[2-(2-methyl-1H-indol-3-yl)ethyl]amino]methyl]phenyl]-2E-2-propenamide free base as shown in FIG. 1. Form $H_B$ is the monohydrate of Form A. Upon heating, it starts decomposing at around 115° C. LOD of around 5.0% corresponds to monohydrate.

In addition, various isolated salt forms of N-hydroxy-3-[4-[[[2-(2-methyl-1H-indol-3-yl)ethyl]amino]methyl]phenyl]-2E-2-propenamide also have been shown to exhibit polymorphism. For example, each of the maleate, hemi-tartarate, mesylate, acetate, benzoate, hemi-fumarate, hemi-malate, phosphate, propionate, sulfate, hemi-succinate and lactate salts exhibit polymorphic forms. As used herein, "salt" refers to a compound prepared by the reaction of an organic acid or base drug with a pharmaceutically acceptable mineral or organic acid or base; suitable pharmaceutically acceptable minerals or organic acids or bases are as listed in Tables 1-8 in *Handbook of Pharmaceutical Salts*, P. H. Stahl and C. G. Wermuth (eds.), VHCA, Zurich 2002, pp. 334-345.

Figure 2:
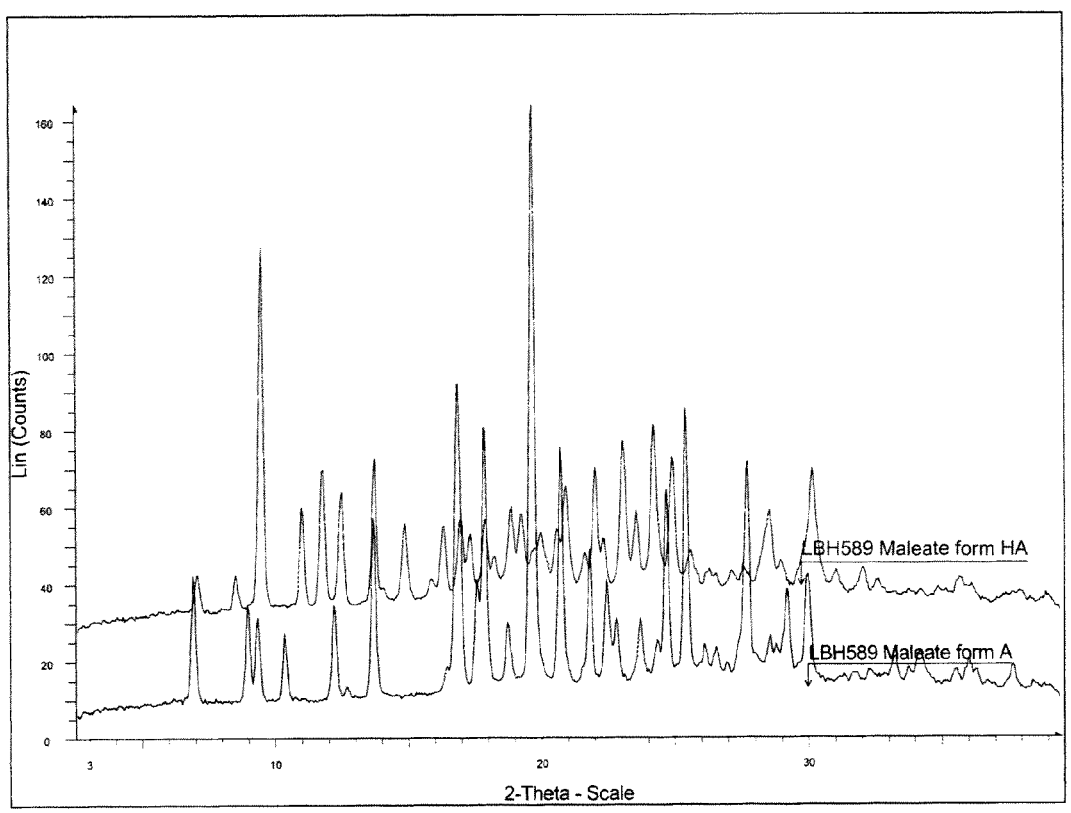
FIG. 2 shows the x-ray powder diffraction patterns for forms A and $H_A$ for the maleate salt of N-hydroxy-3-[4-[[[2-(2-methyl-1H-indol-3-yl)ethyl]amino]methyl]phenyl]-2E-2-propenamide according to the present invention.

Forms A and $H_A$ for the maleate salt can be seen in the XRPD patterns shown in FIG. 2. Forms A, and B and C for the hemi-tartarate salt can be seen in the XRPD patterns shown in FIG. 3. Forms A and B for the mesylate salt can be seen in the XRPD patterns shown in FIG. 4. Forms A and $S_A$ for the acetate salt can be seen in the XRPD patterns shown in FIG. 5. Forms A, $S_A$ and $S_B$ for the benzoate salt can be seen in the XRPD patterns shown in FIG. 6. Forms A, B and $H_A$ for the hemi-fumarate salt can be seen in the XRPD patterns shown in FIG. 7. Forms A and $S_A$ for the hemi-malate salt can be seen in the XRPD patterns shown in FIG. 8. Forms A, $S_A$, $S_B$ and $H_A$ for the phosphate salt can be seen in the XRPD patterns shown in FIG. 9. Forms A and $S_A$ for the propionate salt can be seen in the XRPD patterns shown in FIG. 10. Forms A and $S_A$ for the sulfate salt can be seen in the XRPD patterns shown in FIG. 11. Forms A, B, $H_A$ and $S_A$ for the hemi-succinate salt can be seen in the XRPD patterns shown in FIG. 12. Forms A, $H_A$ and $S_A$ for the DL-lactate salt can be seen in the XRPD patterns shown in FIGS. 13A-13C. Accordingly, additional embodiments of the present invention are directed to each of these substantially pure polymorphic forms of the noted salts of N-hydroxy-3-[4-[[[2-(2-methyl-1H-indol-3-yl)ethyl]amino]methyl]phenyl]-2E-2-propenamide.

Form A of the maleate salt, the only 1:1 salt among dicarboxylic acid salt forming agents, upon heating, decomposes without melting at around 177° C. Its LOD is less than 0.2% at 150° C., and it is nonhygroscopic. The maleate salt has a good aqueous solubility of 2.6 mg/mL and a good intrinsic dissolution. It shows high solubility in methanol and ethanol and considerable solubility in other common organic solvents. Its x-ray powder diffraction pattern shows at least two, more preferably at least four, and most preferably all, maxima selected from 6.9, 8.9, 9.3, 10.3, 13.7, 16.8, 17.8, 19.6, 20.7, 24.7, 25.4 and 27.7 (2θ degrees). A particularly preferred embodiment is directed to a substantially pure polymorphic form A of the maleate salt of N-hydroxy-3-[4-[[[2-(2-methyl-1H-indol-3-yl)ethyl]amino]methyl]phenyl]-2E-2-propenamide as shown in FIG. 2.

Form $H_A$ of the maleate salt, a hydrate of form A, upon heating, decomposes without melting at around 150° C. LOD is around 6.0% at 100° C. Its x-ray powder diffraction pattern shows at least two, more preferably at least four, and most preferably all, maxima selected from 7.0, 8.5, 9.4, 11.0, 11.7, 12.4, 13.7, 23.1, 24.2, 24.9, 28.5 and 30.2 (2θ degrees). A particularly preferred embodiment is directed to a substantially pure polymorphic form $H_A$ of the maleate salt of N-hydroxy-3-[4-[[[2-(2-methyl-1H-indol-3-yl)ethyl]amino]methyl]phenyl]-2E-2-propenamide as shown in FIG. 2.

Figure 3:
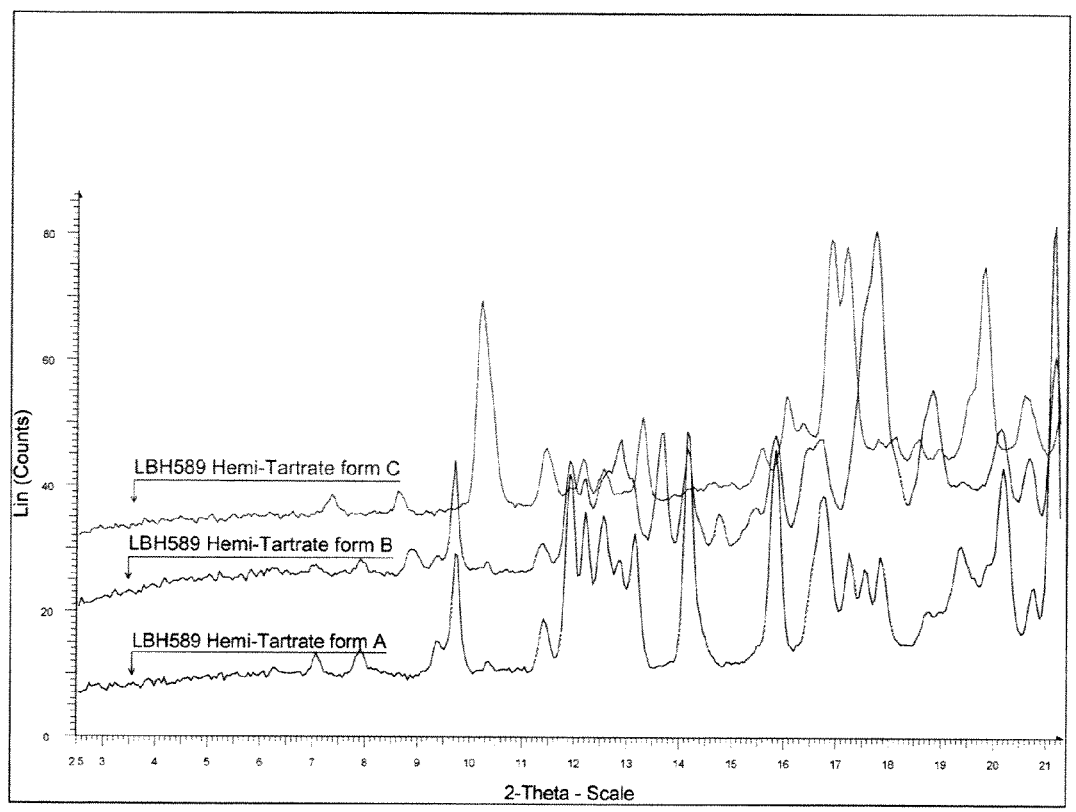
FIG. 3 shows the x-ray powder diffraction patterns for forms A, B and C for the hemi-tartarate salt of N-hydroxy-3-[4-[[[2-(2-methyl-1H-indol-3-yl)ethyl]amino]methyl]phenyl]-2E-2-propenamide according to the present invention.

Form A of the L-tartarate salt, an anhydrous hemi-tartarate, upon heating, decomposes without melting at around 209° C. LOD is less than 0.3% at 150° C., and form A is slightly hygroscopic (less than 0.5% moisture at 85% r.h.). The L-tartarate salt has a good aqueous solubility of 3.5 mg/mL and a good intrinsic dissolution. It shows good solubility in acetone, ethyl acetate and other common organic solvents and limited solubility in alcohols. Upon equilibration, form A converts to form C in methanol, to the chloride salt in 0.1 N HCl, and to the free base in a phosphate buffer (pH=6.8). Its x-ray powder diffraction pattern shows at least two, more preferably at least four, and most preferably all, maxima selected from 9.8, 11.9, 14.2, 15.8, 16.8, 20.2, 21.1, 21.7 and 25.0 (2θ degrees). A particularly preferred embodiment is directed to a substantially pure polymorphic form A of the tartarate salt of N-hydroxy-3-[4-[[[2-(2-methyl-1H-indol-3-yl)ethyl]amino]methyl]phenyl]-2E-2-propenamide as shown in FIG. 3.

Form B of the tartarate salt, also an anhydrous hemi-tartarate, upon heating, decomposes without melting above 160° C. LOD is less than 2.0% at 150° C., indicating its hygroscopic nature. Its x-ray powder diffraction pattern shows at least two, more preferably at least four, and most preferably all, maxima selected from 9.7, 11.9, 13.7, 14.2, 15.8, 17.8, 18.8, 21.2, 21.7, 24.9, 25.9 and 27.9 (2θ degrees). A particularly preferred embodiment is directed to a substantially pure polymorphic form B of the tartarate salt of N-hydroxy-3-[4-[[[2-(2-methyl-1H-indol-3-yl)ethyl]amino]methyl]phenyl]-2E-2-propenamide as shown in FIG. 3.

Form C of the tartarate salt is obtained from equilibration of form A in acetone at ambient temperature. Its x-ray powder diffraction pattern shows maxima at 10.2, 11.5, 13.3, 16.1, 16.9, 17.2, 19.8 (2θ degrees). A particularly preferred embodiment is directed to a substantially pure polymorphic form C of the tartarate salt of N-hydroxy-3-[4-[[[2-(2-methyl-1H-indol-3-yl)ethyl]amino]methyl]phenyl]-2E-2-propenamide as shown in FIG. 3.

Figure 4:
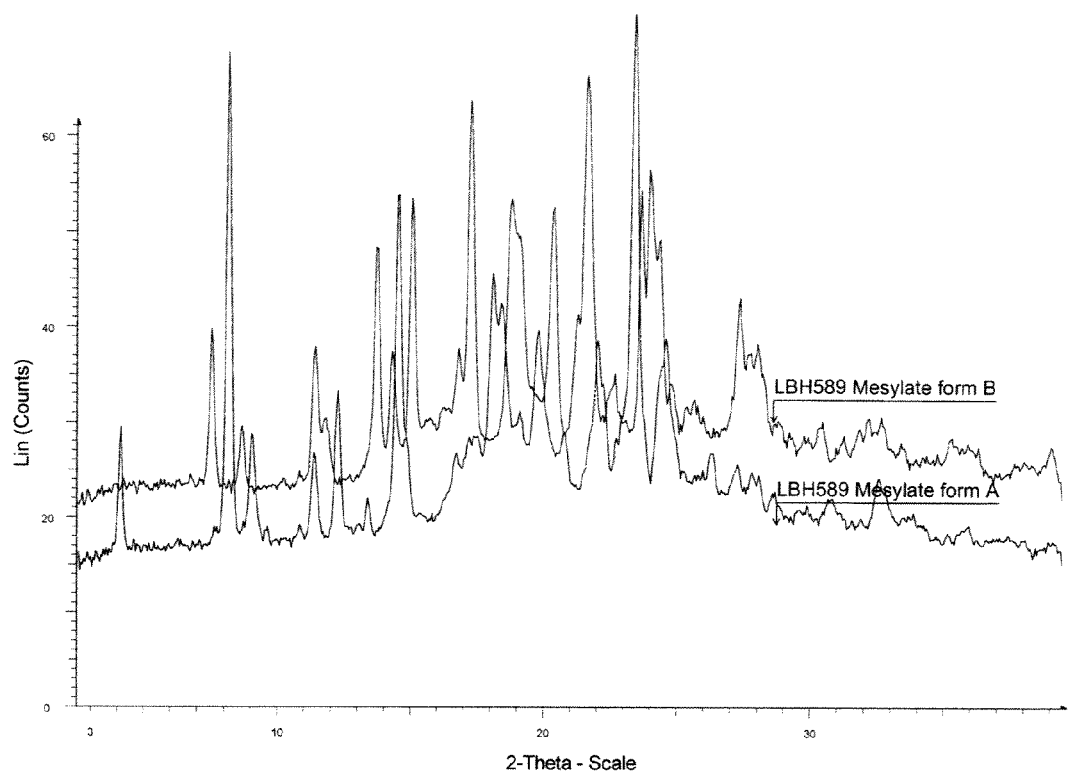
FIG. 4 shows the x-ray powder diffraction patterns for forms A and B of the mesylate (methanesulfonate) salt of N-hydroxy-3-[4-[[[2-(2-methyl-1H-indol-3-yl)ethyl]amino]methyl]phenyl]-2E-2-propenamide according to the present invention.

Form A of the mesylate salt upon heating, decomposes without melting at around 192° C. Its LOD is less than 0.2% at 150° C., and form A is very slightly hygroscopic (less than 0.35% moisture at 85% r.h.). The mesylate salt has an excellent aqueous solubility of 12.9 mg/mL and a high intrinsic dissolution rate. It has high solubility in methanol and ethanol and appreciable solubility in the remaining organic solvents. Upon equilibration, form A converts to form B in water, to the hydrochloride salt in 0.1 N HCl, and to the free base in a phosphate buffer (pH=6.8). Its x-ray powder diffraction pattern shows at least two, more preferably at least four, and most preferably all, maxima selected from 4.1, 8.2, 14.5, 18.1, 18.4, 19.8, 23.5 and 24.6 (2θ degrees). A particularly preferred embodiment is directed to a substantially pure polymorphic form A of the mesylate salt of N-hydroxy-3-[4-[[[2-(2-methyl-1H-indol-3-yl)ethyl]amino]methyl]phenyl]-2E-2-propenamide as shown in FIG. 4.

Form B of the mesylate salt can by obtained from reaction in ethyl acetate at ambient temperature, with subsequent heating of the suspension to 50° C. or from the conversion of form A in water. Its x-ray powder diffraction pattern shows at least two, more preferably at least four, and most preferably all, maxima selected from 7.6, 11.5, 13.8, 15.1, 17.3, 18.9, 20.4, 21.7, 23.7 and 24.0 (2θ degrees). A particularly preferred embodiment is directed to a substantially pure polymorphic form B of the mesylate salt of N-hydroxy-3-[4-[[[2-(2-methyl-1H-indol-3-yl)ethyl]amino]methyl]phenyl]-2E-2-propenamide as shown in FIG. 4.

Figure 5:
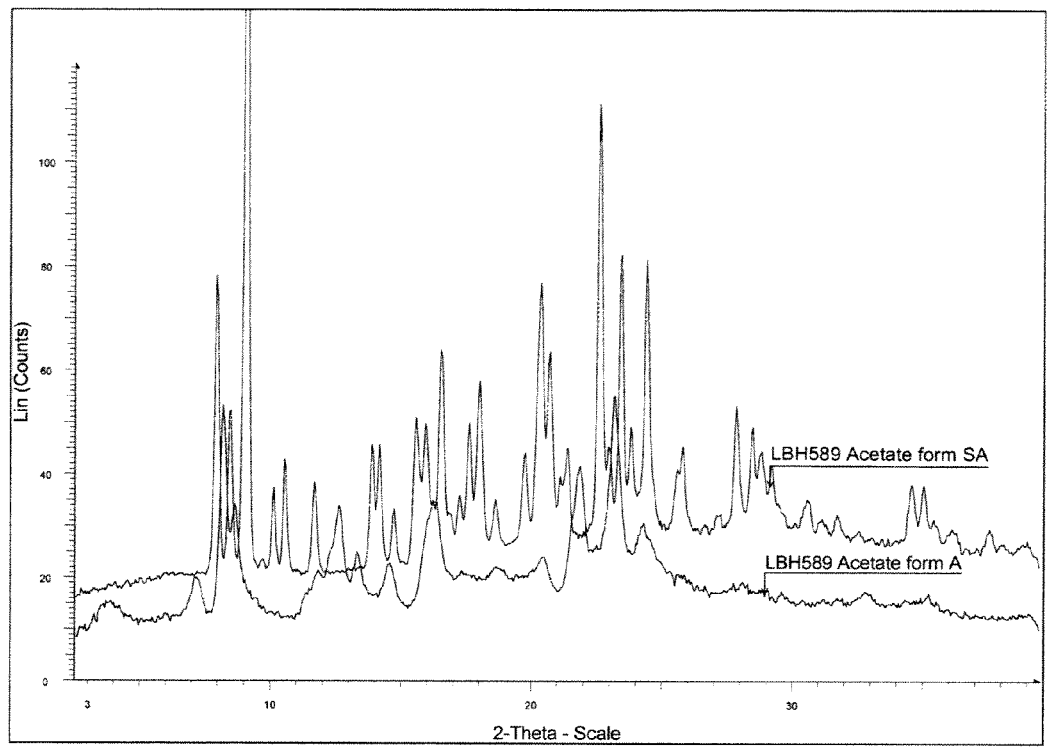
FIG. 5 shows the x-ray powder diffraction patterns for forms A and $S_A$ of the acetate salt of N-hydroxy-3-[4-[[[2-(2-methyl-1H-indol-3-yl)ethyl]amino]methyl]phenyl]-2E-2-propenamide according to the present invention.

Form A of the acetate salt, upon heating, decomposes quickly without melting above 60° C. It has an approximate aqueous solubility of 2 mg/mL. Its x-ray powder diffraction pattern shows at least two, more preferably at least four, and most preferably all, maxima selected from 7.1, 8.2, 8.1, 12.6, 16.3, 21.8 and 23.2 (2θ degrees). A particularly preferred embodiment is directed to a substantially pure polymorphic form A of the acetate salt of N-hydroxy-3-[4-[[[2-(2-methyl-1H-indol-3-yl)ethyl]amino]methyl]phenyl]-2E-2-propenamide as shown in FIG. 5.

Form $S_A$ of the acetate salt is an acetone solvate with the LOD of 13.5% at around 140° C. This solvate is stable below 90° C. Its x-ray powder diffraction pattern shows at least two, more preferably at least four, and most preferably all, maxima selected from 7.9, 8.4, 9.0, 16.5, 20.3, 22.6, 23.4 and 24.4 (2θ degrees). A particularly preferred embodiment is directed to a substantially pure polymorphic form $S_A$ of the acetate salt of N-hydroxy-3-[4-[[[2-(2-methyl-1H-indol-3-yl)ethyl]amino]methyl]phenyl]-2E-2-propenamide as shown in FIG. 5.

Figure 6:
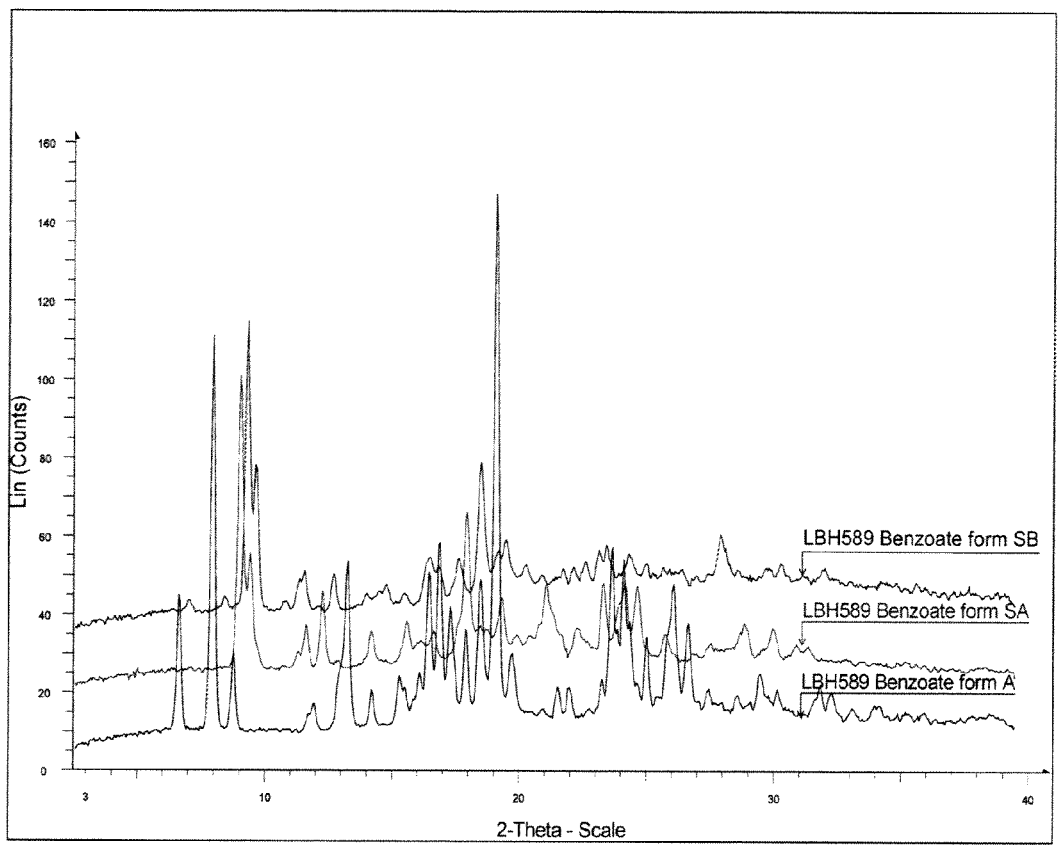
FIG. 6 shows the x-ray powder diffraction patterns for forms A, $S_A$ and $S_B$ of the benzoate salt of N-hydroxy-3-[4-[[[2-(2-methyl-1H-indol-3-yl)ethyl]amino]methyl]phenyl]-2E-2-propenamide according to the present invention.

Form A of the benzoate salt isolated from the reaction in acetone has excellent crystallinity and a high decomposition temperature above 160° C. Its LOD is less than 0.6% at 140° C. It has an approximate aqueous solubility of 0.7 mg/mL. Its x-ray powder diffraction pattern exhibits at least two, more preferably at least four, and most preferably all, maxima selected from 6.6, 7.9, 13.2, 16.4, 16.8, 19.1, 23.6 and 24.1 (2θ degrees). A particularly preferred embodiment is directed to a substantially pure polymorphic form A of the benzoate salt of N-hydroxy-3-[4-[[[2-(2-methyl-1H-indol-3-yl)ethyl]amino]methyl]phenyl]-2E-2-propenamide as shown in FIG. 6.

Form $S_A$ of the benzoate salt is an ethanol solvate with the LOD of 5.2% before decomposition that occurs above 110° C. Its x-ray powder diffraction pattern exhibits at least two, more preferably at least four, and most preferably all, maxima selected from 9.2, 9.6, 11.5, 12.6, 18.5, 19.4, 23.1 and 23.4 (2θ degrees). A particularly preferred embodiment is directed to a substantially pure polymorphic form $S_A$ of the benzoate salt of N-hydroxy-3-[4-[[[2-(2-methyl-1H-indol-3-yl)ethyl] amino]methyl]phenyl]-2E-2-propenamide as shown in FIG. 6.

Form $S_B$ of the benzoate salt is a 2-propanol solvate with the LOD of 6.3% before decomposition that occurs above 100° C. Its x-ray powder diffraction pattern exhibits at least two, more preferably at least four, and most preferably all, maxima selected from 9.3, 11.6, 12.2, 17.9, 21.0, 23.3, 24.1 and 24.6 (2θ degrees). A particularly preferred embodiment is directed to a substantially pure polymorphic form $S_B$ of the benzoate salt of N-hydroxy-3-[4-[[[2-(2-methyl-1H-indol-3-yl)ethyl]amino]methyl]phenyl]-2E-2-propenamide as shown in FIG. 6.

Figure 7:
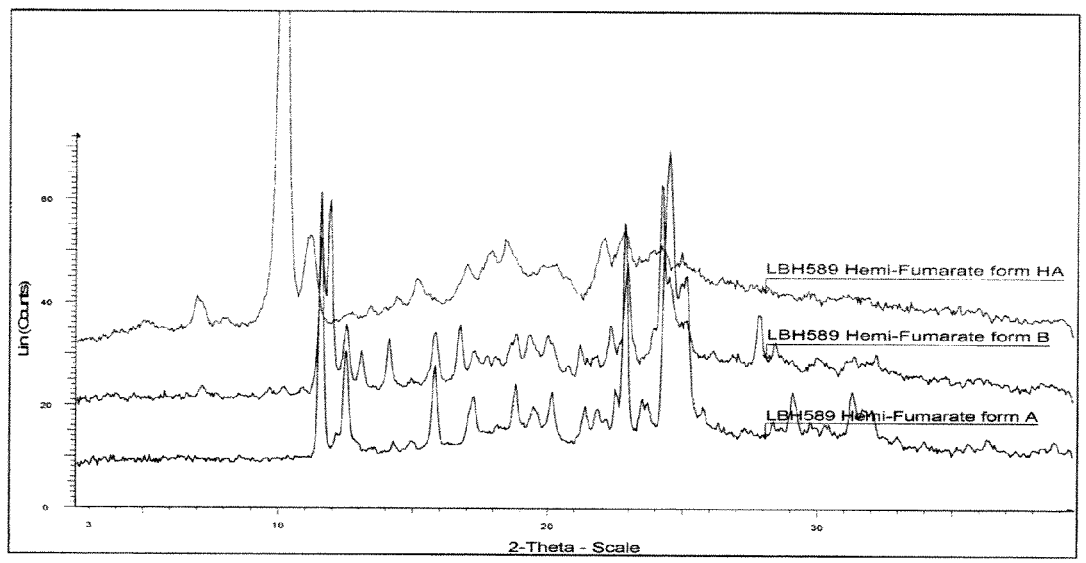
FIG. 7 shows the x-ray powder diffraction patterns for forms A, B and $H_A$ of the hemi-fumarate salt of N-hydroxy-3-[4-[[[2-(2-methyl-1H-indol-3-yl)ethyl]amino]methyl]phenyl]-2E-2-propenamide according to the present invention.

Form A of the hemi-fumarate salt isolated from reaction in ethanol and water (1:0.05) has excellent crystallinity and a high decomposition temperature, 217° C. Its LOD is less than 0.7% at 200° C. It has an approximate aqueous solubility of 0.4 mg/mL. Its x-ray powder diffraction pattern exhibits at least two, more preferably at least four, and most preferably all, maxima selected from 11.5, 12.5, 15.8, 17.2, 18.8, 22.9, 24.5 and 25.0 (2θ degrees). A particularly preferred embodiment is directed to a substantially pure polymorphic form A of the hemi-fumarate salt of N-hydroxy-3-[4-[[[2-(2-methyl-1H-indol-3-yl)ethyl]amino]methyl]phenyl]-2E-2-propenamide as shown in FIG. 7.

Form B of the hemi-fumarate salt isolated from reaction in ethanol has good crystallinity and a decomposition temperature above 160° C. It exhibits a two-step LOD: around 1.1% up to 150° C. and a subsequent 1.7% between 150° C. and 200° C. Its x-ray powder diffraction pattern exhibits at least two, more preferably at least four, and most preferably all, maxima selected from 11.6, 11.9, 12.5, 14.1, 15.8, 22.9, 24.2 and 27.9 (2θ degrees). A particularly preferred embodiment is directed to a substantially pure polymorphic form B of the hemi-fumarate salt of N-hydroxy-3-[4-[[[2-(2-methyl-1H-indol-3-yl)ethyl]amino]methyl]phenyl]-2E-2-propenamide as shown in FIG. 7. It exhibits a two-step LOD: around 3.5% up to 75° C. and a subsequent 6% between 75° C. and 150° C. Its x-ray powder diffraction pattern exhibits at least two, more preferably at least four, and most preferably all, maxima selected from 7.0, 10.1, 11.2, 15.1, 22.1 and 22.8 (2θ degrees). A particularly preferred embodiment is directed to a substantially pure polymorphic form $H_A$ of the hemi-fumarate salt of N-hydroxy-3-[4-[[[2-(2-methyl-1H-indol-3-yl) ethyl]amino]methyl]phenyl]-2E-2-propenamide as shown in FIG. 7.

Figure 8:
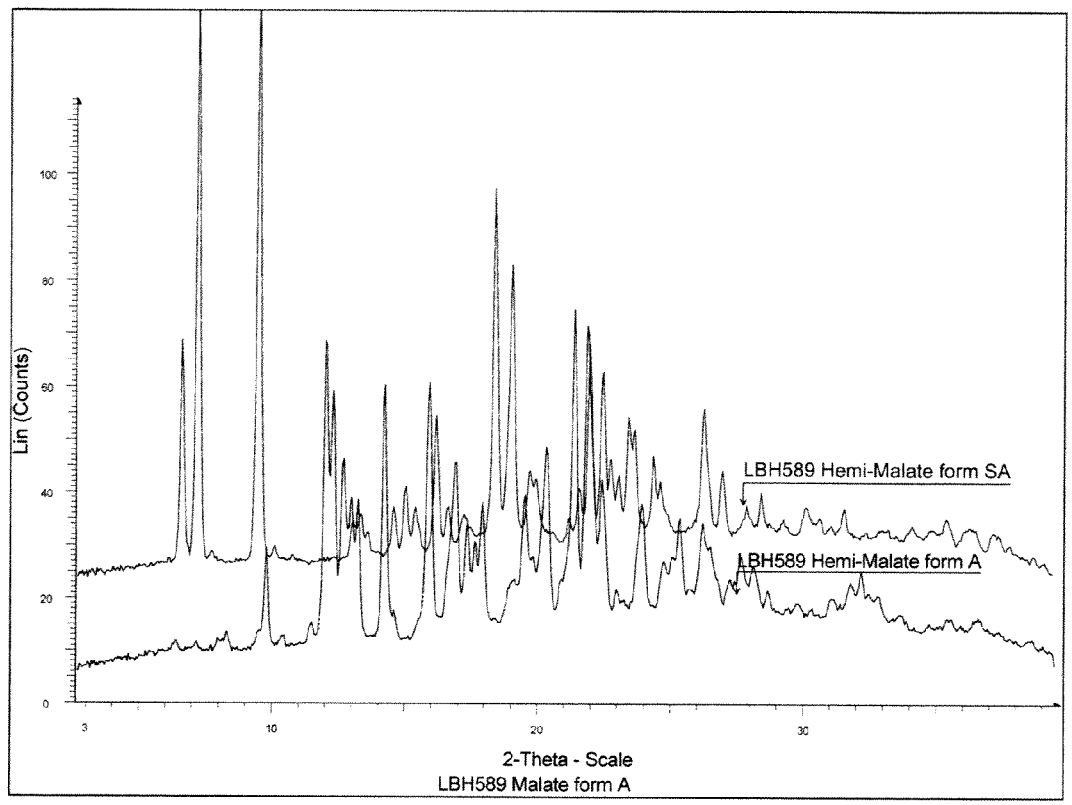
FIG. 8 shows the x-ray powder diffraction patterns for forms A and $S_A$ of the hemi-malate salt of N-hydroxy-3-[4-[[[2-(2-methyl-1H-indol-3-yl)ethyl]amino]methyl]phenyl]-2E-2-propenamide according to the present invention.

Form A of the hemi-malate salt isolated from reaction in ethanol and water (1:0.05) or neat ethanol and 2-propanol, has excellent crystallinity and a high decomposition temperature of 206° C. It exhibits a 2% LOD up to 175° C. It has an approximate aqueous solubility of 1.4 mg/mL. Its x-ray powder diffraction pattern exhibits at least two, more preferably at least four, and most preferably all, maxima selected from 9.7, 12.0, 14.2, 15.9, 16.9, 20.3, 21.4 and 21.9 (2θ degrees). A particularly preferred embodiment is directed to a substantially pure polymorphic form A of the hemi-malate salt of N-hydroxy-3-[4-[[[2-(2-methyl-1H-indol-3-yl)ethyl]amino] methyl]phenyl]-2E-2-propenamide as shown in FIG. 8.

Form $S_A$ of the hemi-malate salt was obtained from the salt formation reaction in acetone. It has excellent crystallinity, but decomposes gradually starting at around 80° C. Its LOD up to 75° C. amounts to 0.6%. Its x-ray powder diffraction pattern exhibits at least two, more preferably at least four, and most preferably all, maxima selected from 6.6, 7.2, 9.4, 16.1, 18.4, 19.0, 21.9 and 22.4 (2θ degrees). A particularly preferred embodiment is directed to a substantially pure polymorphic form $S_A$ of the hemi-malate salt of N-hydroxy-3-[4-[[[2-(2-methyl-1H-indol-3-yl)ethyl]amino]methyl]phenyl]-2E-2-propenamide as shown in FIG. 8.

Figure 9:
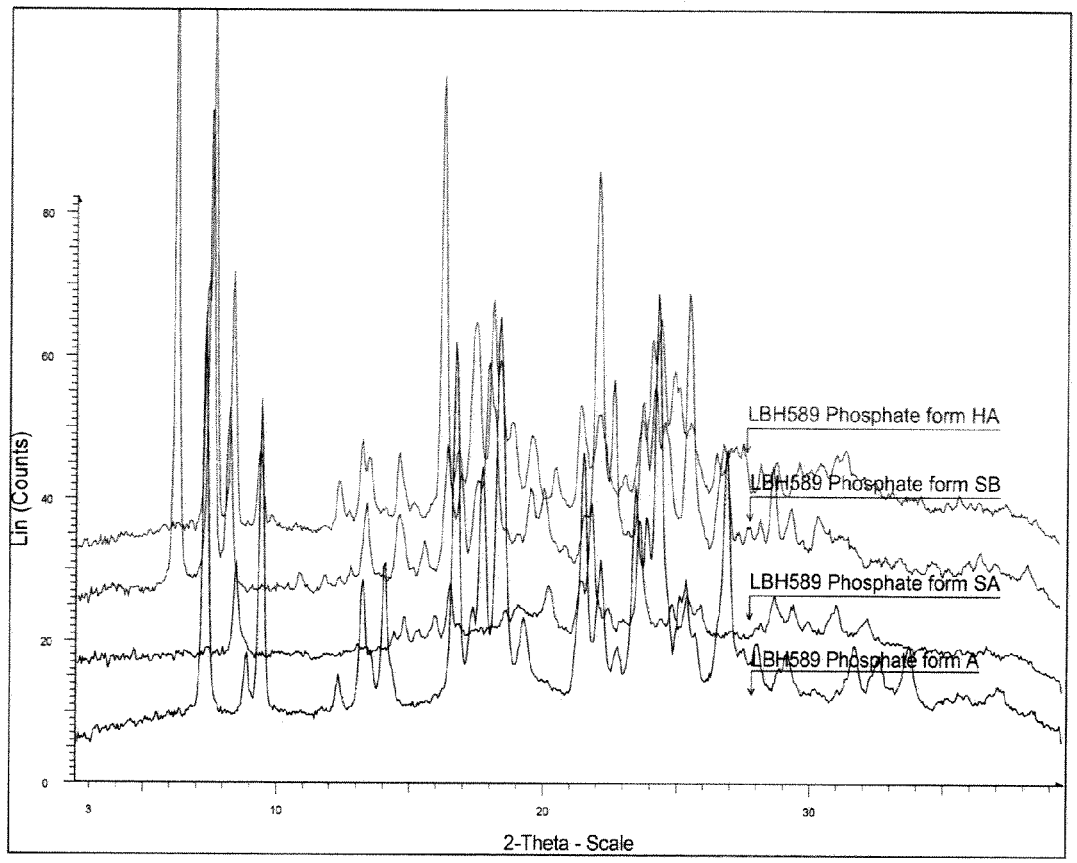
FIG. 9 shows the x-ray powder diffraction patterns for forms A, $S_A$, $S_B$ and $H_A$ of the phosphate salt of N-hydroxy-3-[4-[[[2-(2-methyl-1H-indol-3-yl)ethyl]amino]methyl]phenyl]-2E-2-propenamide according to the present invention.

Form A of the phosphate salt, isolated from reaction in acetone, has excellent crystallinity and a high decomposition temperature of 187° C. It exhibits a 1% LOD up to 165° C. It has an approximate aqueous solubility of 6 mg/mL. Its x-ray powder diffraction pattern exhibits at least two, more preferably at least four, and most preferably all, maxima selected from 7.3, 9.4, 16.7, 17.7, 18.4, 21.5, 24.3 and 26.9 (2θ degrees). A particularly preferred embodiment is directed to a substantially pure polymorphic form A of the phosphate salt of N-hydroxy-3-[4-[[[2-(2-methyl-1H-indol-3-yl)ethyl]amino]methyl]phenyl]-2E-2-propenamide as shown in FIG. 9.

Form $S_A$ of the phosphate salt, isolated from reaction in ethanol, has good crystallinity and exhibits a gradual weight loss on heating. It exhibits a 6.6% LOD up to 150° C. Its x-ray powder diffraction pattern exhibits at least two, more preferably at least four, and most preferably all, maxima selected from 8.4, 16.5, 20.2, 21.8, 23.6, 25.4 and 31.0 (2θ degrees). A particularly preferred embodiment is directed to a substantially pure polymorphic form $S_A$ of the phosphate salt of N-hydroxy-3-[4-[[[2-(2-methyl-1H-indol-3-yl)ethyl]amino]methyl]phenyl]-2E-2-propenamide as shown in FIG. 9.

Form $S_B$ of the phosphate salt, isolated from reaction in 2-propanol, has excellent crystallinity and exhibits a gradual weight loss on heating. It exhibits an around 7% LOD up to 150° C. Its x-ray powder diffraction pattern exhibits at least two, more preferably at least four, and most preferably all, maxima selected from 6.2, 7.5, 8.2, 17.9, 22.1, 22.6, 23.7 and 25.5 (2θ degrees). A particularly preferred embodiment is directed to a substantially pure polymorphic form $S_B$ of the phosphate salt of N-hydroxy-3-[4-[[[2-(2-methyl-1H-indol-3-yl)ethyl]amino]methyl]phenyl]-2E-2-propenamide as shown in FIG. 9.

Form $H_A$ of the phosphate salt, a hydrate, isolated from the reaction in ethanol and water (1:0.05), has excellent crystallinity and a high decomposition temperature of around 180° C. It exhibits a 7% LOD up to 150° C. Its x-ray powder diffraction pattern exhibits at least two, more preferably at least four, and most preferably all, maxima selected from 7.4, 7.6, 8.3, 16.2, 17.4, 18.1 and 24.4 (2θ degrees). A particularly preferred embodiment is directed to a substantially pure polymorphic form $H_A$ of the phosphate salt of N-hydroxy-3-[4-[[[2-(2-methyl-1H-indol-3-yl)ethyl]amino]methyl]phenyl]-2E-2-propenamide as shown in FIG. 9.

Figure 10:
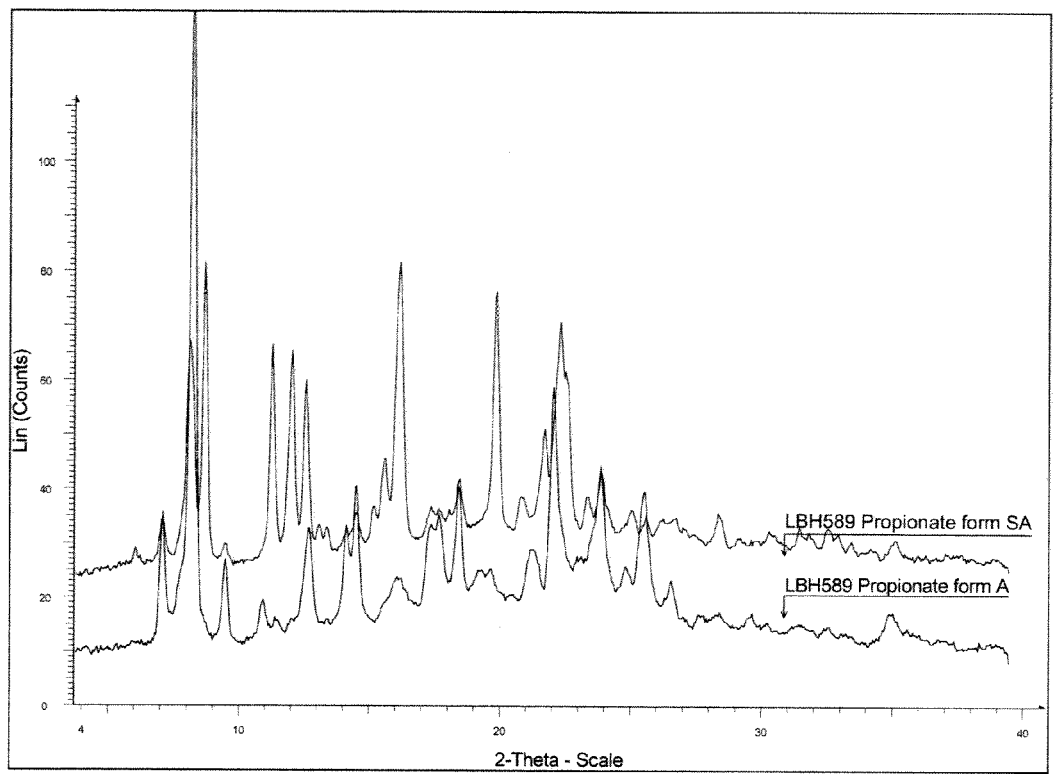
FIG. 10 shows the x-ray powder diffraction patterns for forms A and $S_A$ of the propionate salt of N-hydroxy-3-[4-[[[2-(2-methyl-1H-indol-3-yl)ethyl]amino]methyl]phenyl]-2E-2-propenamide according to the present invention.

Form A of the propionate salt isolated from reaction in acetone has excellent crystallinity; its decomposition temperature is around 99° C. It exhibits an around 7% LOD up to 140° C. It has an approximate aqueous solubility of 4 mg/mL. Its x-ray powder diffraction pattern exhibits at least two, more preferably at least four, and most preferably all, maxima selected from 7.0, 8.2, 9.5, 12.6, 14.1, 14.5, 18.4, 22.0, 23.9 and 25.5 (2θ degrees). A particularly preferred embodiment is directed to a substantially pure polymorphic form A of the propionate salt of N-hydroxy-3-[4-[[[2-(2-methyl-1H-indol-3-yl)ethyl]amino]methyl]phenyl]-2E-2-propenamide as shown in FIG. 10.

Form $S_A$ of the propionate salt, isolated from reaction in 2-propanol, is a 2-propanol solvate with excellent crystallinity. It exhibits a gradual weight loss on heating with an around 15% LOD up to 140° C. Its x-ray powder diffraction pattern exhibits at least two, more preferably at least four, and most preferably all, maxima selected from 7.0, 8.1, 8.7, 11.2, 12.0, 12.5, 16.1, 19.8 and 22.3 (2θ degrees). A particularly preferred embodiment is directed to a substantially pure polymorphic form $S_A$ of the propionate salt of N-hydroxy-3-[4-[[[2-(2-methyl-1H-indol-3-yl)ethyl]amino]methyl]phenyl]-2E-2-propenamide as shown in FIG. 10.

Figure 11:
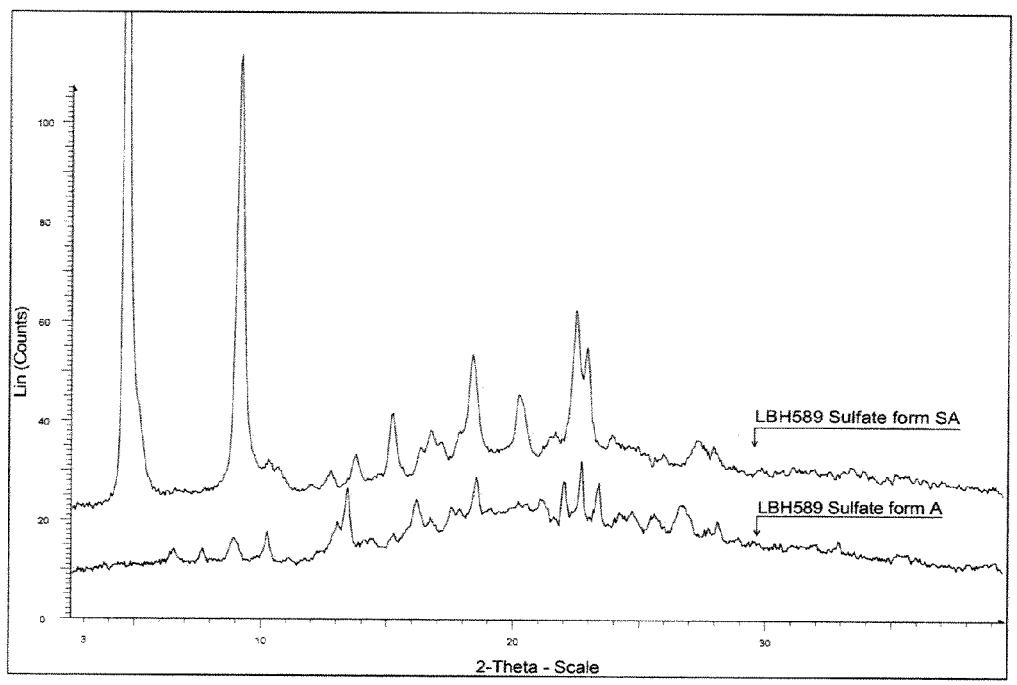
FIG. 11 shows the x-ray powder diffraction patterns for forms A and $S_A$ of the sulfate salt of N-hydroxy-3-[4-[[[2-(2-methyl-1H-indol-3-yl)ethyl]amino]methyl]phenyl]-2E-2-propenamide according to the present invention.

Form A of the sulfate salt isolated from reaction in ethyl acetate as a yellow hygroscopic powder has poor crystallinity, a high decomposition temperature around 160° C., and exhibits an around 7% LOD up to 150° C. It is visibly hygroscopic at ambient conditions. Its x-ray powder diffraction pattern exhibits at least two, more preferably at least four, and most preferably all, maxima selected from 8.9, 10.2, 13.4, 16.1, 18.5, 22.0, 22.7 and 23.4 (2θ degrees). A particularly preferred embodiment is directed to a substantially pure polymorphic form A of the sulfate salt of N-hydroxy-3-[4-[[[2-(2-methyl-1H-indol-3-yl)ethyl]amino]methyl]phenyl]-2E-2-propenamide as shown in FIG. 11.

Form $S_A$ of the sulfate salt, isolated from reaction in 2-propanol, is a 2-propanol solvate with excellent crystallinity and a high decomposition temperature around 162° C. It exhibits an around 9-12% LOD up to 150° C. Its x-ray powder diffraction pattern exhibits at least two, more preferably at least four, and most preferably all, maxima selected from 4.6, 9.1, 13.7, 15.2, 18.4, 20.2, 22.5 and 22.9 (2θ degrees). A particularly preferred embodiment is directed to a substantially pure polymorphic form $S_A$ of the sulfate salt of N-hydroxy-3-[4-[[[2-(2-methyl-1H-indol-3-yl)ethyl]amino]methyl]phenyl]-2E-2-propenamide as shown in FIG. 11.

Figure 12:
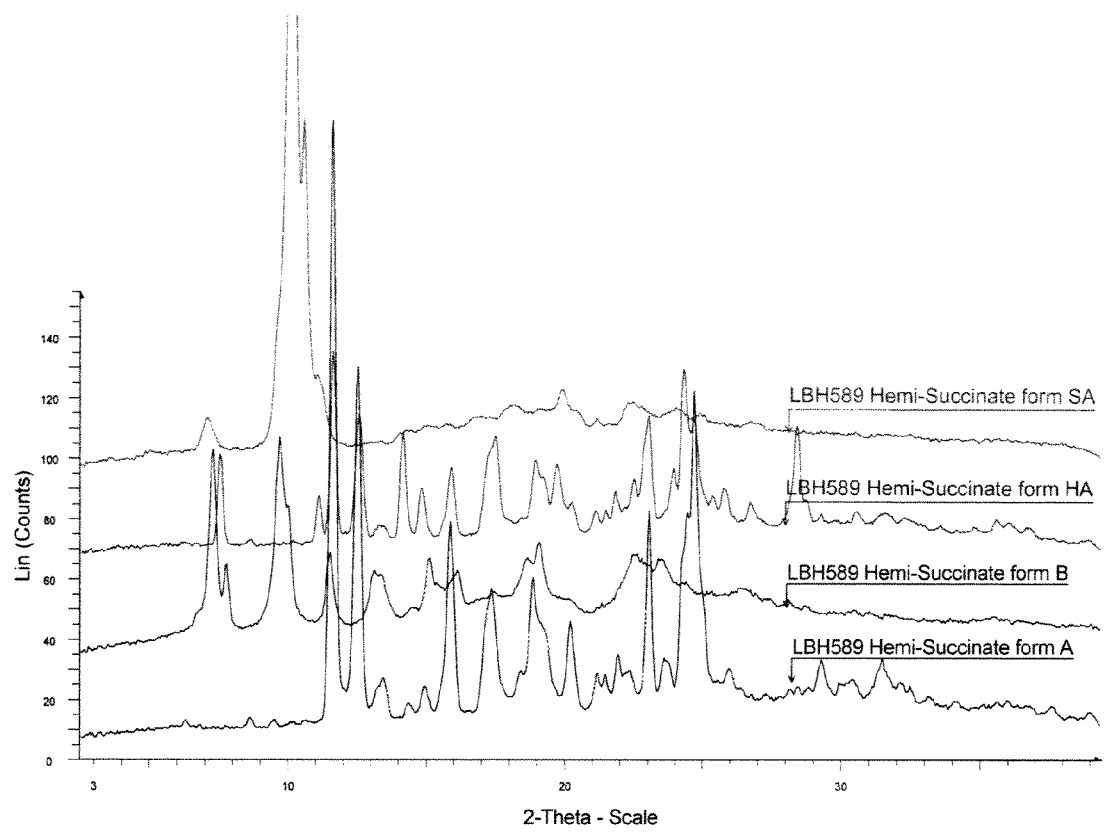
FIG. 12 shows the x-ray powder diffraction patterns for forms A, B, $S_A$ and $H_A$ of the hemi-succinate salt of N-hydroxy-3-[4-[[[2-(2-methyl-1H-indol-3-yl)ethyl]amino]methyl]phenyl]-2E-2-propenamide according to the present invention.

Form A of the hemi-succinate salt reproducibly isolated from reaction in ethanol and water (1:0.05) or neat ethanol has excellent crystallinity and a very high decomposition temperature of around 204° C. It exhibits an around 1.1% LOD up to 200° C. It has an approximate aqueous solubility of 0.4 mg/mL. Its x-ray powder diffraction pattern exhibits at least two, more preferably at least four, and most preferably all, maxima selected from 11.6, 12.5, 15.6, 17.3, 18.8, 23.1 and 24.7 (2θ degrees). A particularly preferred embodiment is directed to a substantially pure polymorphic form A of the hemi-succinate salt of N-hydroxy-3-[4-[[[2-(2-methyl-1H-indol-3-yl)ethyl]amino]methyl]phenyl]-2E-2-propenamide as shown in FIG. 12.

Form B of the hemi-succinate salt, isolated from reaction in acetone or ethyl acetate, has good crystallinity and a high decomposition temperature above 150° C. It exhibits a two-step LOD: around 1.5% up to 125° C. and another 1.3-2.9% up to 150° C. Its x-ray powder diffraction pattern exhibits at least two, more preferably at least four, and most preferably all, maxima selected from 7.2, 7.7, 9.7, 11.5, 13.1, 15.1, 16.1 and 19.1 (2θ degrees). A particularly preferred embodiment is directed to a substantially pure polymorphic form B of the hemi-succinate salt of N-hydroxy-3-[4-[[[2-(2-methyl-1H-indol-3-yl)ethyl]amino]methyl]phenyl]-2E-2-propenamide as shown in FIG. 12.

Form $S_A$ of the hemi-succinate salt, isolated from reaction in 2-propanol, is a 2-propanol solvate with good crystallinity and a high decomposition temperature around 155° C. It exhibits a two-step LOD: around 3% up to 70° C. and another 4.6% up to 140° C. Its x-ray powder diffraction pattern exhibits at least two, more preferably at least four, and most preferably all, maxima selected from 7.0, 10.2, 10.6, 11.1, 18.1 and 19.9 (2θ degrees). A particularly preferred embodiment is directed to a substantially pure polymorphic form $S_A$ of the hemi-succinate salt of N-hydroxy-3-[4-[[[2-(2-methyl-1H-indol-3-yl)ethyl]amino]methyl]phenyl]-2E-2-propenamide as shown in FIG. 12.

Form $H_A$, a monohydrate of the hemi-succinate salt, isolated from reaction in 2-propanol and water (1:0.05), has excellent crystallinity and a high decomposition temperature of around 180° C. It exhibits an around 4.6% LOD up to 160° C., corresponding to monohydrate. Its x-ray powder diffraction pattern exhibits at least two, more preferably at least four, and most preferably all, maxima selected from 7.5, 11.6, 12.5, 14.1, 17.4, 23.0, 24.3 and 28.4 (2θ degrees). A particularly preferred embodiment is directed to a substantially pure polymorphic form $H_A$ of the hemi-succinate salt of N-hydroxy-3-[4-[[[2-(2-methyl-1H-indol-3-yl)ethyl]amino]methyl]phenyl]-2E-2-propenamide as shown in FIG. 12.

Figure 13A:
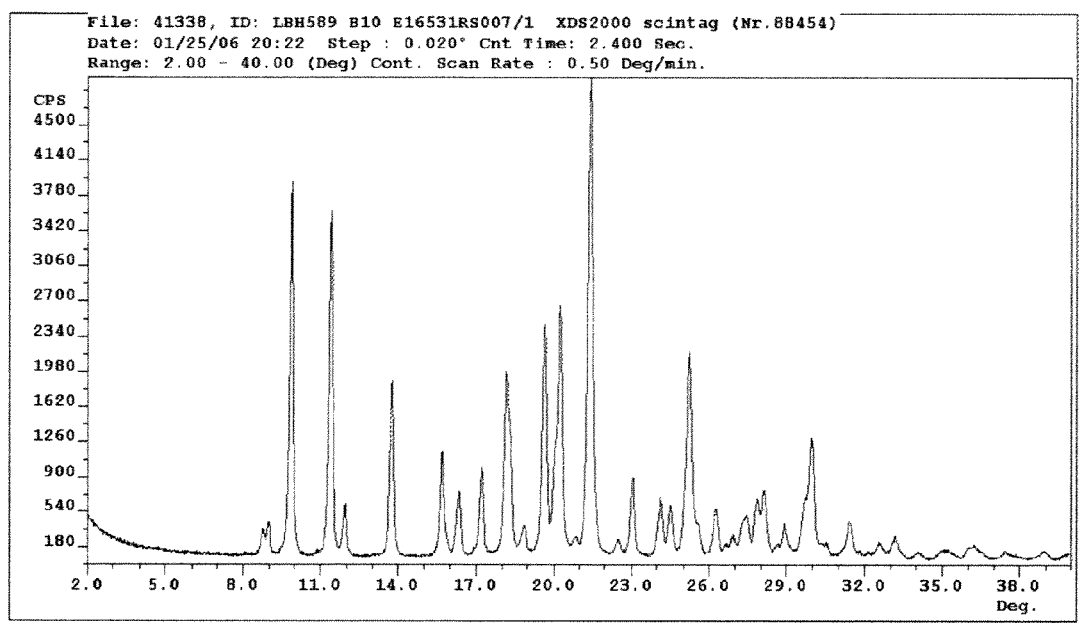
FIGS. 13A, 13B and 13C show the x-ray powder diffraction patterns for forms A, $H_A$ and $S_A$, respectively, of the DL-lactate salt of N-hydroxy-3-[4-[[[2-(2-methyl-1H-indol-3-yl)ethyl]amino]methyl]phenyl]-2E-2-propenamide according to the present invention.

Form A of the DL-lactate salt (anhydrous DL-lactate salt) melts and decomposes at around 183-186° C. and is slightly hygroscopic with a LOD of 0.2% until 120° C. In water and in most organic solvents, form A is more stable than the other forms of the DL-lactate salt. Under most circumstances, form A does not convert into any other form, though upon equilibration at pH 1 and 2, the chloride salt is formed and at 0° C. and 10° C. and in acetone/water mixture, form A was observed along with form $H_A$. Its x-ray powder diffraction pattern exhibits at least two, more preferably at least four, and most preferably all, maxima selected from 9.9, 11.4, 13.8, 15.7, 18.2, 19.7, 20.3, 21.5, 25.3, 27.4 and 30.0 (2θ degrees). A particularly preferred embodiment is directed to a substantially pure polymorphic form A of the DL-lactate salt of N-hydroxy-3-[4-[[[2-(2-methyl-1H-indol-3-yl)ethyl]amino]methyl]phenyl]-2E-2-propenamide as shown in FIG. 13A.

Figure 13B:
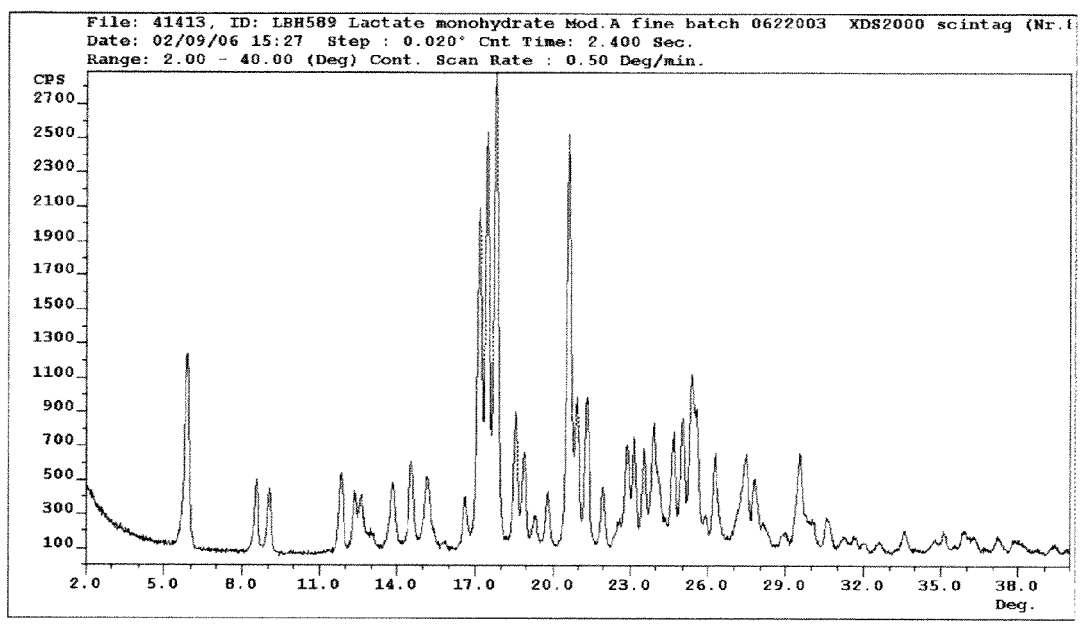

Form $H_A$ of the DL-lactate salt (monohydrate DL-lactate salt) melts and decomposes at around 120° C. and is slightly hygroscopic with a LOD of 0.4% until 110° C., 3.0% until 130° C. and 4.4% until 155° C. (with degradation). Under most circumstances, form $H_A$ slowly converts into form A, though upon equilibration at pH 1 and 2, the chloride salt is formed. Its x-ray powder diffraction pattern exhibits at least two, more preferably at least four, and most preferably all, maxima selected from 5.8, 8.5, 9.0, 11.7, 13.7, 14.5, 15.1, 17.1, 17.4, 17.7, 18.5, 20.5 and 21.2 (2θ degrees). A particularly preferred embodiment is directed to a substantially pure polymorphic form $H_A$ of the DL-lactate salt of N-hydroxy-3-[4-[[[2-(2-methyl-1H-indol-3-yl)ethyl]amino]methyl]phenyl]-2E-2-propenamide as shown in FIG. 13B.

Figure 13C:
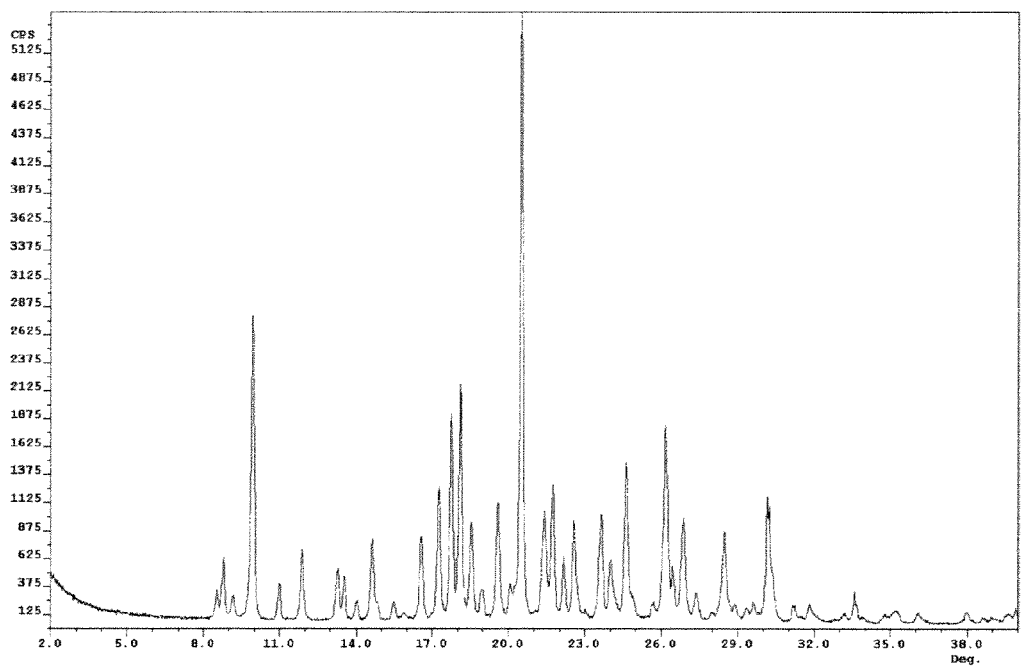

Upon equilibration in methanol, form $H_A$ of the DL-lactate salt converts to form $S_A$ which is a monomethanol solvate of the DL-lactate salt. Form $S_A$ melts and decomposes at around 123° C. with a LOD of 5.9% until 140° C. (with degradation). Its x-ray powder diffraction pattern exhibits at least two, more preferably at least four, and most preferably all, maxima selected from 9.9, 17.2, 17.7, 18.1, 19.5, 20.5, 21.4, 21.7, 22.5, 23.6, 24.6 and 26.1 (2θ degrees). A particularly preferred embodiment is directed to a substantially pure polymorphic form $S_A$ of the DL-lactate salt of N-hydroxy-3-[4-[[[2-(2-methyl-1H-indol-3-yl)ethyl]amino]methyl]phenyl]-2E-2-propenamide as shown in FIG. 13C.

Figure 13D:
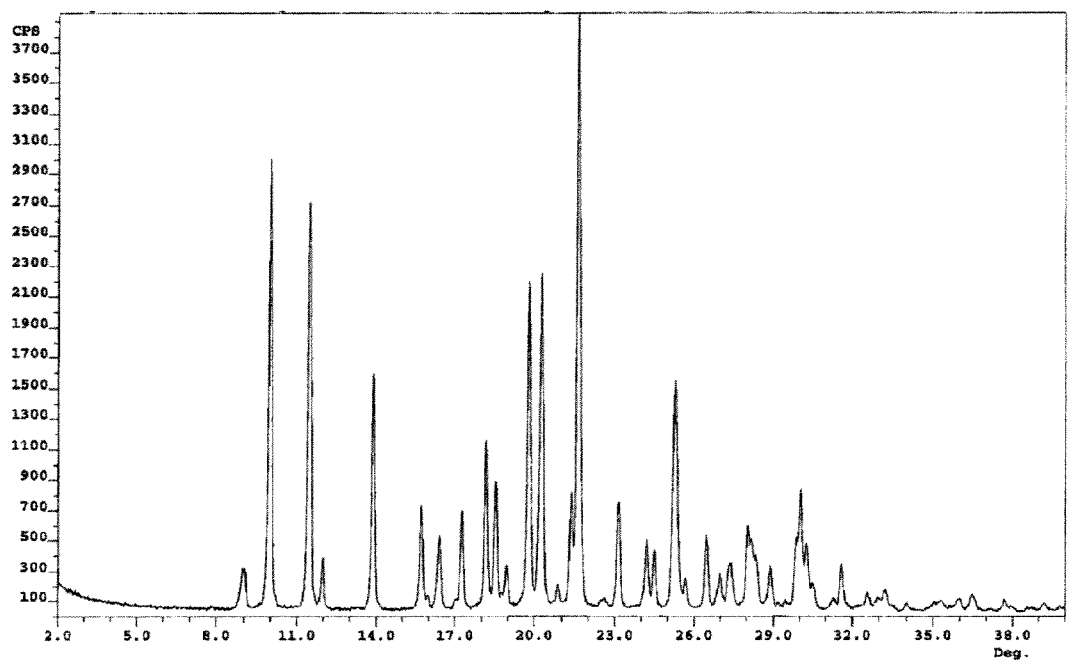
FIGS. 13D and 13E show the x-ray powder diffraction patterns for the anhydrous L-lactate and D-lactate salts, respectively, of N-hydroxy-3-[4-[[[2-(2-methyl-1H-indol-3-yl)ethyl]amino]methyl]phenyl]-2E-2-propenamide.

A particularly preferred embodiment is directed to a substantially pure polymorphic form $S_A$ of the L-(+)-lactate salt of N-hydroxy-3-[4-[[[2-(2-methyl-1H-indol-3-yl)ethyl]amino]methyl]phenyl]-2E-2-propenamide; more preferably, the lactate salt is the anhydrous L-(+)-lactate salt of N-hydroxy-3-[4-[[[2-(2-methyl-1H-indol-3-yl)ethyl]amino]methyl]phenyl]-2E-2-propenamide. The XRPD pattern for the L-(+)-lactate salt of N-hydroxy-3-[4-[[[2-(2-methyl-1H-indol-3-yl)ethyl]amino]methyl]phenyl]-2E-2-propenamide is shown in FIG. 13D. Its x-ray powder diffraction pattern exhibits at least two, more preferably at least four, and most preferably all, maxima selected from 9.9, 11.4, 13.8, 18.1, 18.5, 19.7, 20.2, 21.6, 25.2, and 29.9 (2θ degrees). Melting and decomposition both take place at around 184.7° C. for the L-(+)-lactate salt of N-hydroxy-3-[4-[[[2-(2-methyl-1H-indol-3-yl)ethyl]amino]methyl]phenyl]-2E-2-propenamide anhydrate form.

Figure 13E:
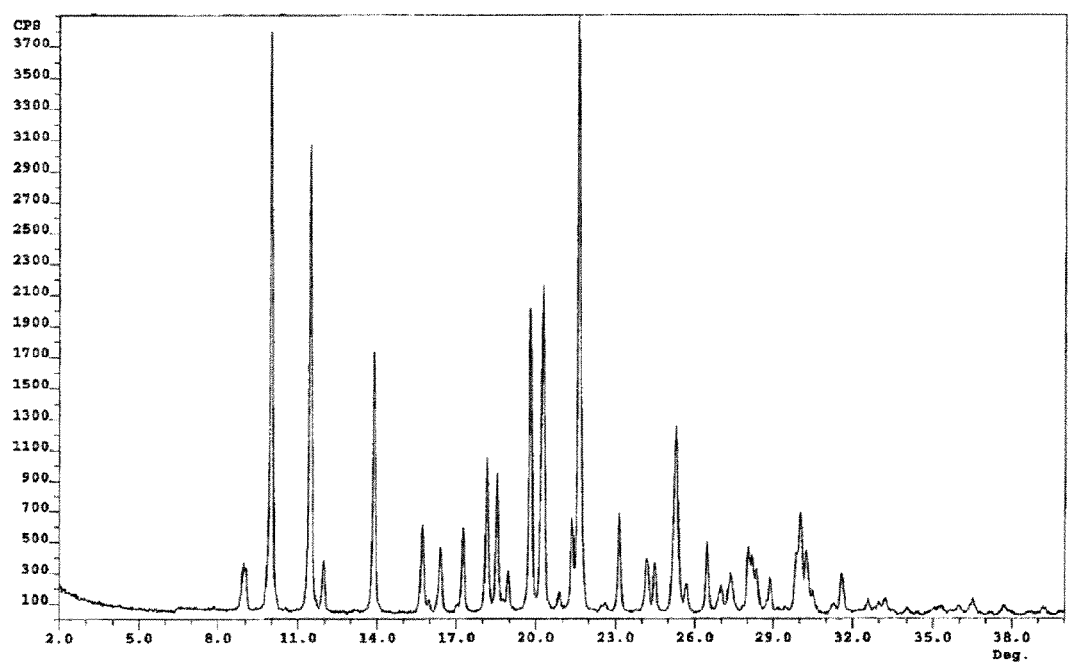

A particularly preferred embodiment is directed to a substantially pure polymorphic form $S_A$ of the D-(−)-lactate salt of N-hydroxy-3-[4-[[[2-(2-methyl-1H-indol-3-yl)ethyl]amino]methyl]phenyl]-2E-2-propenamide; more preferably, the lactate salt is the anhydrous D-(−)-lactate salt of N-hydroxy-3-[4-[[[2-(2-methyl-1H-indol-3-yl)ethyl]amino]methyl]phenyl]-2E-2-propenamide. The XRPD pattern for the D-(−)-lactate salt of N-hydroxy-3-[4-[[[2-(2-methyl-1H-indol-3-yl)ethyl]amino]methyl]phenyl]-2E-2-propenamide is shown in FIG. 13E. Its x-ray powder diffraction pattern exhibits at least two, more preferably at least four, and most preferably all, maxima selected from 9.9, 11.4, 13.8, 18.1, 18.5, 19.7, 20.2, 21.6, and 25.2 (2θ degrees). Melting and decomposition both take place at around 184.1° C. for the D-(−)-lactate salt of N-hydroxy-3-[4-[[[2-(2-methyl-1H-indol-3-yl)ethyl]amino]methyl]phenyl]-2E-2-propenamide anhydrate form Various methods can be used to achieve polymorphic forms of each of the free base and the above-noted salts of N-hydroxy-3-[4-[[[2-(2-methyl-1H-indol-3-yl)ethyl]amino]methyl]phenyl]-2E-2-propenamide. Such methods are as set forth above and as set forth in the below-presented examples.

Another embodiment of the present invention is directed to a pharmaceutical composition comprising:
(a) a therapeutically effective amount of a substantially pure crystalline form of N-hydroxy-3-[4-[[[2-(2-methyl-1H-indol-3-yl)ethyl]amino]methyl]phenyl]-2E-2-propenamide free base or a salt thereof according to one of the earlier embodiments of the present invention; and
(b) at least one pharmaceutically acceptable carrier, diluent, vehicle or excipient.

Preferably, more than 50%, more preferably at least 70%, still more preferably at least 80%, and most preferably at least 90%, of the crystalline form present in the composition is of one of the inventive forms.

A "therapeutically effective amount" is intended to mean the amount of the inventive polymorph that, when administered to a subject in need thereof, is sufficient to effect treatment for disease conditions alleviated by the inhibition of histone deacetylase activity. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The at least one pharmaceutically acceptable carrier, diluent, vehicle or excipient can readily be selected by one of ordinary skill in the art and will be determined by the desired mode of administration. Illustrative examples of suitable modes of administration include oral, nasal, parenteral, topical, transdermal, and rectal. The pharmaceutical compositions of this invention may take any pharmaceutical form recognizable to the skilled artisan as being suitable. Suitable pharmaceutical forms include solid, semisolid, liquid or lyophilized formulations, such as tablets, powders, capsules, suppositories, suspensions, liposomes and aerosols.

Yet another embodiment of the present invention is directed to a method of treating a disease which responds to an inhibition of histone deacetylase activity comprising the step of administering to a subject in need of such treatment a therapeutically effective amount of a substantially pure crystalline form of N-hydroxy-3-[4-[[[2-(2-methyl-1H-indol-3-yl)ethyl]amino]methyl]phenyl]-2E-2-propenamide according to one of the earlier embodiments of the present invention. Preferably, more than 50%, more preferably at least 70%, still more preferably at least 80%, and most preferably at least 90%, of the crystalline form administered is of one of the inventive forms. As noted above, illustrative modes of administration include oral, nasal, parenteral, topical, transdermal and rectal. Administration of the crystalline form may be accomplished by administration of a pharmaceutical composition of this invention or via any other effective means.

Specific embodiments of the invention will now be demonstrated by reference to the following examples. It should be understood that these examples are disclosed solely by way of illustrating the invention and should not be taken in any way to limit the scope of the present invention.

In the following examples, with regard to crystallinity, "excellent" refers to a material having XRPD main peaks which are sharp and have intensities above 70 counts; "good" refers to a material having XRPD main peaks which are sharp and have intensities within 30-70 counts; and "poor" refers to a material having XRPD main peaks which are broad and have intensities below 30 counts. In addition, LOD refers to weight loss determined between ambient and decomposition temperatures. The later is approximated by the onset of the first derivative of the thermogravimetric curve vs. temperature. This is not the true onset, since weight loss does not occur with the same rate for all the salts. Hence, the actual decomposition temperature may be lower than that stated. Salt formation, stoichiometry, and the presence or absence of solvents is confirmed by observing the $^1$H-NMR chemical shifts of the corresponding salt forming agents and reaction solvents (the tables contain one characteristic chemical shift for salt forming agents or solvents). Water content could not be extracted from the NMR data, because the water peaks were broad. The extent of protonation of the free base is assessed by the change in the chemical shift of the benzylic ($H_{bz}$) protons. Further, salts of the present invention precipitated out as free-flowing powders (FFP), sticky amorphous materials (SAM) (which had a gummy consistency that tended to agglomerate, forming a single spherical mass or stick to the walls of the reaction vessel) or amorphous gels (AG). Finally, "-" indicates a measurement not taken.

Example 1

Preparation of Acetate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 1. A stoichiometric amount of acetic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 1

| Solvent | T, ° C. | Physical Appearance | Crystallinity and Form | LOD, % $T_{decomposition}$ ($T_{desolvation}$) | $^1$H-NMR |
|---|---|---|---|---|---|
| Acetone | Ambient | FFP | Excellent $S_A$ | 13.5 (107.9) 147.9 | 1.89 (acetate, 3H) 2.08 (acetone, 6H) 3.74 ($H_{bz}$) |
| IPA | 60 | FFP | Good A | ~10.5 (72.5) 148.7 | — |
| AcOEt | 60 | FFP | Good A | 9.3 (105.1) 147.9 | 1.89 (acetate, 3H) 3.73 ($H_{bz}$) |

The salt forming reaction in acetone produced a highly crystalline salt, with the ratio of N-hydroxy-3-[4-[[[2-(2-methyl-1H-indol-3-yl)ethyl]amino]methyl]phenyl]-2E-2-propenamide to acetate of 1:1 identified as a stoichiometric acetone solvate $S_A$. The salt forming reaction in isopropyl alcohol and ethyl acetate at 60° C. produced the same crystalline, non-solvated acetate salt (form A). The accompanied weight loss above 105° C. is either due to the loss of water or loss of acetic acid or both.

Example 2

Preparation of Benzoate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 2. A stoichiometric amount of benzoic acid was subsequently added to the suspension. The mixture was stirred at ambient temperature (where a clear solution formed, stirring continued at 4° C.). Solids were collected by filtration and analyzed by XRPD, TGA and in some instances $^1$H-NMR.

TABLE 2

| Solvent | T, ° C. | Physical Appearance | Crystallinity and Form | LOD, % $T_{decomposition}$ | $^1$H-NMR |
|---|---|---|---|---|---|
| EtOH:H$_2$O (1:0.05) | Ambient | FFP | Excellent $S_A$ | 1.5 prior to dec. at 110° C. | — |
| IPA:H$_2$O (1:0.05) | Ambient | FFP | Excellent $S_B$ | 6.3* (isothermal at 120° C.) | 1.02 (IPA, 6H) 3.83 ($H_{bz}$) |

TABLE 2-continued

| Solvent | T, °C. | Physical Appearance | Crystallinity and Form | LOD, % $T_{decomposition}$ | $^1$H-NMR |
|---|---|---|---|---|---|
| EtOH | Ambient | FFP | Excellent $S_A$ | 5.2* (isothermal at 120° C.) | 1.04 (EtOH, 5H) 3.43 (EtOH, 1H) 7.93 (benzoate, 2H) 3.85 ($H_{bz}$) |
| IPA | Ambient | FFP | Excellent $S_B$ | 1.5% prior dec. at 100° C. | — |
| Acetone | Ambient | FFP | Excellent A | 0.5% 160.2 | 7.93 (benzoate, 2H) 3.84 ($H_{bz}$) |

*Isothermal hold at 120° C. for 10 minutes

The salt forming reaction in ethanol alone and with water produced the same ethanol solvate $S_A$. The stoichiometry of the protonated base:benzoate:ethanol is 1:1:0.5 by NMR. Solvent loss and decomposition are closely spaced events at the heating rate of 10° C./min, and the ethanol content could not be determined initially. Eventually, it was determined by holding at 120° C. for 10 minutes. The LOD of 5.2% corresponds to 0.5 moles of ethanol per formula unit. Isopropyl alcohol alone and with water produced the same isopropanol (IPA) solvate $S_B$. The stoichiometry of the protonated base:benzoate is 1:1 by NMR. Solvent loss and decomposition are closely spaced at the heating rate of 110° C./min., and the isopropanol content could not be determined initially. Eventually, it was determined by holding at 120° C. for 10 minutes. The 6.3% LOD corresponds to 0.5 moles of IPA per formula unit. Based on solvent content and XRPD patterns, the two solvates $S_A$ and $S_B$ appeared to be isostructural. The salt forming reaction in acetone produced benzoate salt that did not contain any solvent or water, a 1:1 stoichiometric salt of excellent crystallinity and high decomposition temperature (form A).

Example 3

Formation of Hemi-Fumarate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 3. A stoichiometric amount of fumaric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 3

| Solvent | T, °C. | Physical Appearance | Crystallinity and Form | LOD, % $T_{decomposition}$ | $^1$H-NMR |
|---|---|---|---|---|---|
| EtOH | Ambient | FFP to SAM to FFP | excellent B | 1.1 + 1.7 (2-step) 213.2 | 3.93 ($H_{bz}$) 6.50 (1H, fumarate) |
| IPA | Ambient | FFP | consists of one intense peak $H_A$ | 3.4 + 6.0 (2-step) 159.8 | 3.91 ($H_{bz}$) 6.50 (1H, fumarate) only small amount of IPA |
| EtOH:H$_2$O (1:0.05) | Ambient | FFP to SAM to FFP | Excellent A | 0.7 217.4 | 3.90 ($H_{bz}$) 6.49 (1H, fumarate) |
| IPA:H$_2$O (1:0.05) | Ambient | FFP | Excellent A | 1.5 208.2 | — |
| IPA:H$_2$O (1:0.05) | Ambient | FFP | Excellent A | — | — |
| EtOH:H$_2$O (1:0.025) | Ambient | FFP to SAM to FFP | Poor A | 0.7 154.8 | — |
| EtOH:H$_2$O (1:0.05) | Ambient | FFP to SAM to FFP | Excellent A | 0.9 217.1 | 3.90 ($H_{bz}$) 6.49 (1H, fumarate) |

The salt forming reactions in isopropyl alcohol and acetone at ambient temperature produced fumarate salt of stoichiometry 2:1 (protonated base:fumarate), i.e., hemi-fumarate salts. Although none of them was a solvate, they had poor crystallinity and a low decomposition temperature. The LOD for isopropyl alcohol at ambient temperature was most likely associated with the loss of water (most likely $H_A$ form). The salt forming reaction in ethanol, ethanol and water, and isopropyl alcohol and water, all at ambient temperature or 60° C., produced a fumarate salt of stoichiometry 2:1 (protonated base:fumarate)), i.e., hemi-fumarate salt. The salt forming reaction in ethanol and water and isopropyl alcohol and water (1:0.05), ambient or 60° C., produced identical XRPD spectra (anhydrous form A). The spectrum of the salt formed by ethanol at ambient temperature, albeit similar, displays some small differences and it may represent a unique, hemi-fumarate polymorph (form B) of similar structure.

Example 4

Formation of Maleate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 4. A stoichiometric amount of maleic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 4

| Solvent | T, ° C. | Physical Appearance | Crystallinity and Form | LOD, % $T_{decomposition}$ | $^1$H-NMR |
|---------|---------|---------------------|------------------------|----------------------------|-----------|
| EtOH | RT to 4 | Clear solut. to FFP | Excellent $H_A$? | 6.2 (RT) 150 | 4.22 ($H_{bz}$) 6.01 (2H, maleate) |
| IPA | 60 | SAM to FFP | Excellent A | 0.2 178.1 | 4.22 ($H_{bz}$) 6.01 (2H, maleate) |
| Acetone | 60 | SAM to FFP | Excellent A | 0.2 176.1 | 4.22 ($H_{bz}$) 6.01 (2H, maleate) |

The salt forming reaction in isopropyl alcohol and acetone at 60° C. produced highly crystalline, anhydrous solids that decompose above ~180° C. Maleic acid was the only dicarboxylic acid that produced a 1:1 salt with N-hydroxy-3-[4-[[[2-(2-methyl-1H-indol-3-yl)ethyl]amino]methyl]phenyl]-2E-2-propenamide. Its H-NMR spectrum displays a resonance at 6.01 ppm, corresponding to the two olefinic protons, and a resonance at 10.79 ppm due to one unprotonated carboxylic acid. Maleic acid also formed a salt with high water content that is lost under mild heating conditions. It is likely that the salt forming reaction in ethanol (RT to 4° C.) produced a hydrate (form $H_A$).

Example 5

Formation of Hemi-Malate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 5. A stoichiometric amount of malic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 5

| Solvent | T, ° C. | Physical Appearance | Crystallinity and Form | LOD, % $T_{decomposition}$ | $^1$H-NMR |
|---------|---------|---------------------|------------------------|----------------------------|-----------|
| EtOH:H$_2$O (1:0.05) | 60 | SAM to FFP | Excellent A | 1.9 206.0 | 3.96 ($H_{bz}$) 3.83 (0.5H, malate) |
| EtOH | 60 | SAM to FFP | Excellent A | 0.4 199.3 | — |
| IPA | 60 | SAM to FFP | Excellent A | — | — |
| Acetone | 60 | SAM to FFP | Excellent $S_A$ | 0.6 95 | 3.97 ($H_{bz}$) 3.84 (0.5H, malate) |
| EtOH:H$_2$O (1:0.05) | Ambient | SAM to FFP | Excellent A | — | — |

The salt forming reaction in ethanol and water, ethanol and isopropyl alcohol produced the same crystalline and anhydrous hemi-malate salt. The difference in LOD between ethanol and water (1:0.05) and ethanol may reflect varying amounts of amorphous material in the two samples. The salt forming reaction in acetone afforded a different hemi-malate salt that continuously loses weight above ~95° C. This salt is an acetone solvate (form $S_A$). Solvent loss and decomposition are closely spaced thermal events.

Example 6

Formation of Mesylate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 6. A stoichiometric amount of methanesulfonic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 6

| Solvent | T, °C. | Physical Appearance | Crystallinity and Form | LOD, % $T_{decomposition}$ | $^1$H-NMR |
|---|---|---|---|---|---|
| Acetone | 60 | SAM to FFP | Excellent A + B ? | 1.6 172.8 | 4.22 ($H_{bz}$) 2.33 (~5H, methane sulfonate) |
| AcOEt | Ambient | FFP | Excellent A | 1.3 + 1.3 (2-step) 170.9 | 4.22 ($H_{bz}$) 2.36 (~5H, methane sulfonate) |

The salt forming reaction in ethyl acetate afforded a yellow salt, upon stirring at room temperature. The salt (form A) is crystalline, displays a 2-step weight loss and, by NMR, does not contain any solvent but appears to have more than one molecule of methanesulfonate (mesylate). The salt forming reaction in acetone afforded isolation of a white powder after heating at 60° C. It displayed excellent crystallinity but may be a composite of more than one polymorphic form (forms A and B). By NMR, it does not contain any solvent but appears to contain more than one molecule of methanesulfonate. Another salt forming reaction in ethyl acetate, in which reaction is initiated at ambient temperature and then the obtained yellowish powder suspension is heated to 50° C., afforded isolation of a new form B, as shown in FIG. 4.

Example 7

Formation of Phosphate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 7. A stoichiometric amount of phosphoric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 7

| Solvent | T, °C. | Physical Appearance | Crystallinity and Form | LOD, % $T_{decomposition}$ | $^1$H-NMR |
|---|---|---|---|---|---|
| EtOH:H$_2$O (1:0.05) | 60 | FFP | Excellent H$_A$ | 7.0 179.6 | 3.94 ($H_{bz}$) |
| EtOH | Ambient | FFP | Good S$_A$ | ~6.6 | 1.1 (~1.5H, EtOH) 4.00 ($H_{bz}$) |
| IPA | Ambient | FFP | Excellent S$_B$ | ~7.0 | 1.02 (3-4H, IPA) 4.00 ($H_{bz}$) |
| Acetone | RT to 60 | SAM to FFP | Excellent A | 1.0 187.4 | 4.00 ($H_{bz}$) |
| AcOEt | RT to 60 | SAM to FFP | Good A | 1.2 175.5 | — |

The salt forming reaction in ethanol and isopropyl alcohol gave ethanol and isopropanol hemi-solvates (forms S$_A$ and S$_B$ respectively). In ethanol and water, only traces of ethanol were detected by NMR, in spite of the large LOD. The material is either hygroscopic or a hydrate (form H$_A$) that loses water upon gentle heating and vacuum conditions (the loss of water measured by TGA is complete in by ~60° C. at 10° C./min.). The salt forming reaction in acetone and ethyl acetate produced the same crystalline and anhydrous phosphate salt (form A). The stoichiometry is most likely 1:1. The salt displays a high decomposition temperature.

Example 8

Formation of Propionate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 8. A stoichiometric amount of propionic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 8

| Solvent | T, °C. | Physical Appearance | Crystallinity and Form | LOD, % $T_{decomposition}$ | $^1$H-NMR |
|---|---|---|---|---|---|
| IPA | 60 | FFP | Excellent S$_A$ | 15.1 | 0.97 (3H, propionic) 1.02 (~4H, IPA) 3.73 ($H_{bz}$) |
| Acetone | 60 | FFP | Excellent A | 7.0 98.9 | 0.97 (3H, propionic) 3.73 (Hbz) |
| AcOEt | 60 | FFP | Excellent A | 6.3 ~100 | — |

A salt forming reaction in ethanol afforded the unreacted free base (most likely form H$_B$). Isopropyl alcohol produced an IPA solvate of the propionate salt (form S$_A$). Based on NMR, the IPA content is ~0.5. The salt shows a weight loss of 15%, which corresponds to the loss of IPA plus an unidentified component. The salt forming reaction in acetone and ethyl acetate produced the same crystalline and unsolvated salt (form A). A weight loss of 6.3-7%, that starts at ~100° C., is due to water, propionic acid or a decomposition product. Upon completion of weight loss (~140° C.), the salt decomposes. It should be pointed out that when the material is dissolved in DMSO for NMR, free propionic acid and only traces of propionate were detected.

Example 9

Formation of Sulfate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 9. A stoichiometric amount of sulfuric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 9

| Solvent | T, ° C. | Physical Appearance | Crystallinity and Form | LOD, % $T_{decomposition}$ | $^1$H-NMR |
|---|---|---|---|---|---|
| IPA | 60 | SAM to FFP | Excellent $S_A$ | 8.9 to 12 162 | 1.02 (6H, IPA) 1.10 (3H, IPA$^+$) 4.22 ($H_{bz}$) |
| AcOEt | Ambient | FFP | Poor A | ~6.7 ~160 | 4.22 ($H_{bz}$) |

The salt forming reaction in isopropyl alcohol afforded isolation of a white crystalline salt. It was identified as an isopropanol solvate (form $S_A$), containing 1.5 mol of IPA per formula unit. In DMSO, 0.5 mol of IPA is protonated. The salt forming reaction in ethyl acetate afforded isolation of a yellow hygroscopic powder (form A). During filtration, the sample visibly absorbed moisture, and its poor crystallinity is attributed to this effect.

Example 10

Formation of Hemi-Succinate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 10. A stoichiometric amount of succinic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 10

| Solvent | T, ° C. | Physical Appearance | Crystallinity and Form | LOD, % $T_{decomposition}$ | $^1$H-NMR |
|---|---|---|---|---|---|
| EtOH:H$_2$O (1:0.05) | 60 | SAM to FFP | Excellent A | 1.1 203.7 | 2.31 (2H, succinate) 3.86 ($H_{bz}$) |
| IPA:H$_2$O (1:0.05) | 60 | SAM to FFP | Excellent $H_A$ | 4.6 | 2.31 (2H, succinate) 3.85 ($H_{bz}$) |
| EtOH | Ambient | FFP to SAM to FFP | Excellent A | 1.1 194.6 | 2.31 (2H, succinate) 3.85 ($H_{bz}$) |
| IPA | Ambient | FFP | Good $S_A$ | 2.8 + 4.6 (90.6) (2-step) 155.8 | 1.02 (~3H, IPA) 2.32 (2H, succinate) 3.88 ($H_{bz}$) |
| Acetone | Ambient | FFP | Good B | 1.5 + 1.3 (2-step) 162.3 | 2.31 (2H, succinate) 3.86 ($H_{bz}$) |
| AcOEt | Ambient | FFP | Good B | 1.3 + 2.9 154.5 | — |
| EtOH | 60 | SAM to FFP | Excellent A | — | — |
| EtOH:H$_2$O (1:0.025) | 60 | SAM to FFP | Excellent A | 1.0 197.3 | 2.31 (2H, succinate) 3.85 ($H_{bz}$) |
| EtOH:H$_2$O (1:0.05) | 60 | SAM to FFP | Excellent A | — | — |

Four distinctly different hemi-succinate salts were isolated: a monohydrate (form A) (ethanol at ambient), a hemisolvate of isopropanol (form $S_A$) (isopropyl alcohol), and two unsolvated forms A and B. Form A displays higher crystallinity, minimal weight loss up to 200° C., and higher decomposition temperature. In addition, it could be synthesized reproducibly, as demonstrated in ethanol and ethanol and water at 60° C.

Example 11

Formation of Hemi-L-Tartarate Salt

About 40-50 mg of N-hydroxy-3-[4-[[[2-(2-methyl-1H-indol-3-yl)ethyl]amino]methyl]phenyl]-2E-2-propenamide free base monohydrate was suspended in 1 mL of a solvent as listed in Table 11. A stoichiometric amount of tartaric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 11

| Solvent | T, ° C. | Physical Appearance | Crystallinity and Form | LOD, % $T_{decomposition}$ | $^1$H-NMR |
|---|---|---|---|---|---|
| EtOH:H$_2$O (1:0.05) | RT to 60 | FFP to SAM to FFP | Excellent A | 0.5 206.9 | 3.86 (1H, tartarate) 3.95 (H$_{bz}$) |
| EtOH:H$_2$O (1:0.025) | 60 | SAM to FFP | Excellent A | — | — |
| EtOH:H$_2$O (1:0.05) | 60 | SAM to FFP | Excellent A | 0.5 207.6 | 3.86 (1H, tartarate) 3.95 (H$_{bz}$) |
| EtOH | 60 | SAM to FFP | Excellent A | — | — |
| IPA:H$_2$O (1:0.05 | 60 | SAM to FFP | Good B | 1.9 and 3.4 >160° C. | 3.90 (1H, tartarate) 3.96 (H$_{bz}$) |

The salt forming reaction of the free base with tartaric acid required heating to elevated temperatures. A highly crystalline, anhydrous salt that decomposed above 200° C. was isolated as a hemi-tartarate and was labeled as form A. Form B was isolated once in isopropyl alcohol and water at 60° C. and, although very similar in structure with A, significant differences were seen in its XRPD pattern.

Example 12

Formation of L-Tartarate Salt 3.67 g (10 mmol) of the free base monohydrate (N-hydroxy-3-[4-[[[2-(2-methyl-1H-indol-3-yl)ethyl]amino]methyl]phenyl]-2E-2-propenamide) and 50 mL of absolute ethanol were charged in a 250 mL 3-neck flask equipped with a magnetic stirrer and an addition funnel. The mixture was heated to 60° C., and to the hot suspension were added dropwise 0.83 g (5.5 mmol, 10% excess) of L-tartaric acid dissolved in 15 mL absolute ethanol. Initially, large yellow agglomerates formed that prevented adequate stirring, but overtime these were converted to free flowing and stirrable yellow powder. Stirring continued at 60° C. for 2 hours. The mixture was subsequently cooled to room temperature and placed in an ice bath for approximately 30 minutes. The yellow powder was recovered by filtration and washed once by cold absolute ethanol (10 mL). It was dried overnight under vacuum to yield 4.1 g of the L-tartarate (hemi-tartarate) salt of N-hydroxy-3-[4-[[[2-(2-methyl-1H-indol-3-yl)ethyl]amino]methyl]phenyl]-2E-2-propenamide (96.6%).

Example 13

Formation of Mesylate Salt 3.67 g (10 mmol) of the free base monohydrate (N-hydroxy-3-[4-[[[2-(2-methyl-1H-indol-3-yl)ethyl]amino]methyl]phenyl]-2E-2-propenamide) and 75 mL of ethyl acetate were charged in a 250 mL 3-neck flask equipped with a mechanical stirrer and an addition funnel. To the stirred suspension were added dropwise 0.65 mL (10 mmol) of methane sulfonic acid dissolved in 20 mL of ethyl acetate, affording a stirrable suspension of a free flowing yellow powder. The mixture was heated to 50° C. and kept there overnight, and during that time the yellow powder converted to a white solid. The suspension was cooled to room temperature and the white solid was recovered by filtration. It was washed once with cold ethyl acetate (15 mL) and dried overnight under vacuum to yield 4.38 g of the mesylate salt of N-hydroxy-3-[4-[[[2-(2-methyl-1H-indol-3-yl)ethyl]amino]methyl]phenyl]-2E-2-propenamide (98.3%).

It is noted that the initially formed yellow powder is a form of the mesylate salt that contains more than the equimolar amount of methane sulfonic acid. As a result, this solid is very highly hygroscopic. Upon gentle heating to 40° C. or 50° C. and within 2-4 hours the yellow powder converts to a white crystalline solid that contains the equimolar amount of the methane sulfonic acid. This salt is non-hygroscopic. It is also advised that addition of the methane sulfonic acid is done at ambient temperature and the temperature increased afterwards. It was observed that addition at higher temperature afforded the immediate precipitation of the salt as a soft and gummy material.

Example 14

Formation of Maleate Salt 3.67 g (10 mmol) of the free base monohydrate (N-hydroxy-3-[4-[[[2-(2-methyl-1H-indol-3-yl)ethyl]amino]methyl]phenyl]-2E-2-propenamide) and 75 mL of acetone were charged in a 250 mL 3-neck flask equipped with a mechanical stirrer and an addition funnel. The mixture was heated to 45° C., and to the hot suspension were added dropwise 1.16 g (10 mmol) of maleic acid dissolved in 25 mL acetone. Although the addition was slow, the salt precipitated out as a soft gummy solid hindering stirring. Stirring continued overnight at 45° C. and during that time the solid converted to a white free-flowing powder. The mixture was cooled to room temperature and placed in an ice bath for approximately 30 minutes. The white solid was recovered by filtration, washed once with cold acetone (15 mL), and dried overnight under vacuum to yield 4.21 g of the maleate salt of N-hydroxy-3-[4-[[[2-(2-methyl-1H-indol-3-yl)ethyl]amino]methyl]phenyl]-2E-2-propenamide (90.5%).

It is noted that a more preferable solvent for synthesis is 2-propanol. During optimization, however, it was observed that, in addition to the desired form, another polymorph with a low decomposition temperature (118.9° C.) could be isolated from 2-propanol as a yellow powder.

Example 15

Formation of Anhydrous DL-Lactate Salt

DL-lactic acid (4.0 g, 85% solution in water, corresponding to 3.4 g pure DL-lactic acid) is diluted with water (27.2 g), and the solution is heated to 90° C. (inner temperature) for 15 hours. The solution is allowed to cool down to room temperature and is used as lactic acid solution for the following salt formation step.

N-hydroxy-3-[4-[[[2-(2-methyl-1H-indol-3-yl)ethyl]amino]methyl]phenyl]-2E-2-propenamide free base form $H_A$ (10.0 g) is placed in a 4-necked reaction flask with mechanical stirrer. Demineralized water (110.5 g) is added, and the suspension is heated to 65° C. (inner temperature) within 30 minutes. The DL-lactic acid solution is added to this suspension during 30 minutes at 65° C. During the addition of the lactate salt solution, the suspension converted into a solution. The addition funnel is rinsed with demineralized water (9.1 g), and the solution is stirred at 65° C. for an additional 30 minutes. The solution is cooled down to 45° C. (inner temperature) and seed crystals (10 mg N-hydroxy-3-[4-[[[2-(2-methyl-1H-indol-3-yl)ethyl]amino]methyl]phenyl]-2E-2-propenamide DL-lactate monohydrate) are added at this temperature. The suspension is cooled down to 33° C. and is stirred for an additional 20 hours at this temperature. The suspension is re-heated to 65° C., stirred for 1 hour at this temperature and is cooled to 33° C. within 1 hour. After additional stirring for 3 hours at 33° C., the product is isolated by filtration, and the filter cake is washed with demineralized water (2×20 g). The wet filter-cake is dried in vacuo at 50° C. to obtain the anhydrous N-hydroxy-3-[4-[[[2-(2-methyl-1H-indol-3-yl)ethyl]amino]methyl]phenyl]-2E-2-propenamide DL-lactate salt as a crystalline product. The product is identical to the monohydrate salt (form $H_A$) in HPLC and in $^1$H-NMR, with the exception of the integrals of water signals in the $^1$H-NMR spectra. XRPD indicated the presence of the anhydrate form.

In additional salt formation experiments carried out according to the procedure described above, the product solution was filtered at 65° C. before cooling to 45° C., seeding and crystallization. In all cases, form A (anhydrate form) was obtained as product.

Example 16

Formation of Anhydrous DL-Lactate Salt

DL-lactic acid (2.0 g, 85% solution in water, corresponding to 1.7 g pure DL-lactic acid) is diluted with water (13.6 g), and the solution is heated to 90° C. (inner temperature) for 15 hours. The solution was allowed to cool down to room temperature and is used as lactic acid solution for the following salt formation step.

N-hydroxy-3-[4-[[[2-(2-methyl-1H-indol-3-yl)ethyl]amino]methyl]phenyl]-2E-2-propenamide free base form $H_A$ (5.0 g) is placed in a 4-necked reaction flask with mechanical stirrer. Demineralized water (54.85 g) is added, and the suspension is heated to 48° C. (inner temperature) within 30 minutes. The DL-lactic acid solution is added to this suspension during 30 minutes at 48° C. Seed crystals are added (as a suspension of 5 mg N-hydroxy-3-[4-[[[2-(2-methyl-1H-indol-3-yl)ethyl]amino]methyl]phenyl]-2E-2-propenamide DL-lactate salt, anhydrate form A, in 0.25 g of water) and stirring is continued for 2 additional hours at 48° C. The temperature is raised to 65° C. (inner temperature) within 30 minutes, and the suspension is stirred for an additional 2.5 hours at this temperature. Then the temperature is cooled down to 48° C. within 2 hours, and stirring is continued at this temperature for an additional 22 hours. The product is isolated by filtration and the filter cake is washed with demineralized water (2×10 g). The wet filter-cake is dried in vacuo at 50° C. to obtain anhydrous N-hydroxy-3-[4-[[[2-(2-methyl-1H-indol-3-yl)ethyl]amino]methyl]phenyl]-2E-2-propenamide DL-lactate salt (form A) as a crystalline product. Melting point and decomposition take place together at 183.3° C.

Example 17

Conversion of DL-Lactate Salt Monohydrate to DL-Lactate Salt Anhydrate

DL-lactic acid (0.59 g, 85% solution in water, corresponding to 0.5 g pure DL-lactic acid) is diluted with water (4.1 g), and the solution is heated to 90° C. (inner temperature) for 15 hours. The solution is allowed to cool down to room temperature and is used as lactic acid solution for the following salt formation step.

10 g of N-hydroxy-3-[4-[[[2-(2-methyl-1H-indol-3-yl)ethyl]amino]methyl]phenyl]-2E-2-propenamide DL-lactate salt monohydrate form $H_A$ is placed in a 4-necked reaction flask. Water (110.9 g) is added, followed by the addition of the lactic acid solution. The addition funnel of the lactic acid is rinsed with water (15.65 g). The suspension is heated to 82° C. (inner temperature) to obtain a solution. The solution is stirred for 15 minutes at 82° C. and is hot filtered into another reaction flask to obtain a clear solution. The temperature is cooled down to 50° C., and seed crystals are added (as a suspension of 10 mg N-hydroxy-3-[4-[[[2-(2-methyl-1H-indol-3-yl)ethyl]amino]methyl]phenyl]-2E-2-propenamide DL-lactate salt, anhydrate form, in 0.5 g of water). The temperature is cooled down to 33° C. and stirring is continued for an additional 19 hours at this temperature. The formed suspension is heated again to 65° C. (inner temperature) within 45 minutes, stirred at 65° C. for 1 hour and cooled down to 33° C. within 1 hour. After stirring at 33° C. for an additional 3 hours, the product is isolated by filtration, and the wet filter cake is washed with water (50 g). The product is dried in vacuo at 50° C. to obtain crystalline anhydrous N-hydroxy-3-[4-[[[2-(2-methyl-1H-indol-3-yl)ethyl]amino]methyl]phenyl]-2E-2-propenamide DL-lactate salt (form A).

Example 18

Formation of Anhydrous DL-Lactate Salt

DL-lactic acid (8.0 g, 85% solution in water, corresponding to 6.8 g pure DL-lactic acid) was diluted with water (54.4 g), and the solution was heated to 90° C. (inner temperature) for 15 hours. The solution was allowed to cool down to room temperature and was used as lactic acid solution for the following salt formation step.

N-hydroxy-3-[4-[[[2-(2-methyl-1H-indol-3-yl)ethyl]amino]methyl]phenyl]-2E-2-propenamide free base form $H_A$ (20 g) is placed in a 1 L glass reactor, and ethanol/water (209.4 g of a 1:1 w/w mixture) is added. The light yellow suspension is heated to 60° C. (inner temperature) within 30 minutes, and the lactic acid solution is added during 30 minutes at this temperature. The addition funnel is rinsed with water (10 g). The solution is cooled to 38° C. within 2 hours, and seed crystals (2θ mg of N-hydroxy-3-[4-[[[2-(2-methyl-1H-indol-3-yl)ethyl]amino]methyl]phenyl]-2E-2-propenamide DL-lactate salt, anhydrate form) are added at 38° C. After stirring at 38° C. for an additional 2 hours, the mixture is cooled down to 25° C. within 6 hours. Cooling is continued from 25° C. to 10° C. within 5 hours, from 10° C. to 5° C. within 4 hours and from 5° C. to 2° C. within 1 hour. The suspension is stirred for an additional 2 hours at 2° C., and the product is isolated by filtration. The wet filter cake is washed with water (2×30 g), and the product is dried in vacuo at 45° C. to obtain crystalline anhydrous N-hydroxy-3-[4-[[[2-(2-methyl-1H-indol-3-yl)ethyl]amino]methyl]phenyl]-2E-2-propenamide DL-lactate salt (form A).

Example 19

Formation of DL-Lactate Monohydrate Salt 3.67 g (10 mmol) of the free base form $H_A$ (N-hydroxy-3-[4-[[[2-(2-methyl-1H-indol-3-yl)ethyl]amino]methyl]phenyl]-2E-2-propenamide) and 75 mL of acetone were charged in a 250 mL 3-neck flask equipped with a magnetic stirrer and an addition funnel. To the stirred suspension were added dropwise 10 mL of 1 M lactic acid in water (10 mmol) dissolved in 20 mL acetone, affording a clear solution. Stirring continued at ambient and a white solid precipitated out after approximately 1 hour. The mixture was cooled in an ice bath and stirred for an additional hour. The white solid was recovered by filtration and washed once with cold acetone (15 mL). It was subsequently dried under vacuum to yield 3.94 g of the DL-lactate monohydrate salt of N-hydroxy-3-[4-[[[2-(2-methyl-1H-indol-3-yl)ethyl]amino]methyl]phenyl]-2E-2-propenamide (86.2%).

Example 20

Formation of Monohydrate DL-Lactate Salt

About 40-50 mg of N-hydroxy-3-[4-[[[2-(2-methyl-1H-indol-3-yl)ethyl]amino]methyl]phenyl]-2E-2-propenamide free form $H_A$ was suspended in 1 mL of a solvent as listed in Table 12. A stoichiometric amount of lactic acid was subsequently added to the suspension. The mixture was stirred at ambient temperature and when a clear solution formed, stirring continued at 4° C. Solids were collected by filtration and analyzed by XRPD, TGA and $^1$H-NMR.

TABLE 12

| Solvent | T, ° C. | Physical Appearance | Crystallinity and Form | LOD, % $T_{decomposition}$ | $^1$H-NMR |
|---------|---------|---------------------|------------------------|---------------------------|-----------|
| IPA | 4 | FFP | Excellent $H_A$ | 4.3 (79.3) 156.3 | — |
| Acetone | 4 | FFP | Excellent $H_A$ | 4.5 (77.8) 149.5 | 4.18 ($H_{bz}$) |

The salt forming reaction in isopropyl alcohol and acetone at 4° C. produced a stoichiometric (1:1) DL-lactate salt, a monohydrate. The salt is crystalline, begins to dehydrate above 77° C., and decomposes above 150° C.

Example 21

Formation of Anhydrous L-(+)-Lactate Salt

N-hydroxy-3-[4-[[[2-(2-methyl-1H-indol-3-yl)ethyl]amino]methyl]phenyl]-2E-2-propenamide free base (20.0 g) was treated with L-(+)-lactic acid (6.8 g) according to the procedure described in Example 19 to obtain crystalline N-hydroxy-3-[4-[[[2-(2-methyl-1H-indol-3-yl)ethyl]amino]methyl]phenyl]-2E-2-propenamide L-(+)-lactate salt, anhydrate form. Melting point and decomposition take place together at 184.7° C. The XRPD pattern is as shown in FIG. 13D (2θ=9.9, 11.4, 13.8, 18.1, 18.5, 19.7, 20.2, 21.6, 25.2, 29.9).

Example 22

Formation of Anhydrous D-(−)-Lactate Salt

N-hydroxy-3-[4-[[[2-(2-methyl-1H-indol-3-yl)ethyl]amino]methyl]phenyl]-2E-2-propenamide free base (20.0 g) was treated with D-(−)-lactic acid (6.8 g) according to the procedure described in Example 19 to obtain crystalline N-hydroxy-3-[4-[[[2-(2-methyl-1H-indol-3-yl)ethyl]amino]methyl]phenyl]-2E-2-propenamide D-(−)-lactate salt, anhydrate form. Melting point and decomposition take place together at 184.1° C. The XRPD pattern is as shown in FIG. 13E (2θ=9.9, 11.4, 13.8, 18.1, 18.5, 19.7, 20.2, 21.6, 25.2).

| | Morphic Properties | | | | | | | |
|---|---|---|---|---|---|---|---|---|
| Parameter | Free Base | | L-Tartarate | | Mesylate | | Maleate | |
| As is | | | | | | | | |
| DSC | Not applicable | | Not applicable | | Not applicable | | Not applicable | |
| XRPD (crystallinity) | Excellent | | Excellent | | Excellent | | Excellent | |
| Sample RH % | Sorption | Desorption | Sorption | Desorption | Sorption | Desorption | Sorption | Desorption |
| 1.5 | 0.00 | NA | 0.00 | NA | 0.00 | NA | 0.00 | NA |
| 5 | 0.06 | 4.11 | 0.04 | −0.09 | 0.03 | −0.03 | 0.02 | −0.02 |
| 25 | 3.39 | 5.11 | 0.11 | 0.03 | 0.10 | 0.07 | 0.07 | 0.05 |
| 50 | 5.17 | 5.21 | 0.20 | 0.16 | 0.16 | 0.16 | 0.12 | 0.10 |
| 75 | 5.22 | 5.31 | 0.31 | 0.36 | 0.23 | 0.25 | 0.16 | 0.17 |
| 85 | 5.24 | 5.33 | 0.35 | 0.42 | 0.31 | 0.33 | 0.17 | 0.19 |
| 95 | 5.37 | 5.37 | 0.49 | 0.49 | 0.82 | 0.82 | 0.21 | 0.21 |

-continued

| Parameter | Morphic Properties | | | |
|---|---|---|---|---|
| | Free Base | L-Tartarate | Mesylate | Maleate |
| | XRPD | XRPD | XRPD | XRPD |
| Methanol | Changed to new form (A) | Changed to new | NA form (C) | No change |
| Ethanol | Changed to new form (A) | No change | No change | No change |
| 2-Propanol | No change | No change | No change | No change |
| Acetone | No change | No change | No change | No change |
| Ethyl Acetate | No change | No change | No change | No change |
| Water | No change | No change | Changed to new form (B) | No change |
| 0.1 N HCl | Converted to hydrochloride salt | Converted to hydrochloride salt | Converted to hydrochloride salt | Converted to hydrochloride salt |
| pH = 6.8 buffer | No change | Converted to free base ($H_A$) | Converted to free base ($H_A$) | No change |
| | Blocks | Agglomerates of irregular blocks | NA | Blocks and microcrystalline powder |

Sorption-desorption isotherms were recorded by a VTI humidity balance. The salts of (N-hydroxy-3-[4-[[[2-(2-methyl-1H-indol-3-yl)ethyl]amino]methyl]phenyl]-2E-2-propenamide were first subjected to a drying step (25° C., r.h. below 2%, 2 hours) and then to a sorption-desorption-sorption sequence, with each RH % step retained for 3 hours. The free base was kept below 2% r.h. for several hours, and thus was completely dehydrated after the drying step. Only the data of the first sorption cycle are given in the table, since, in all cases, the two sorption cycles were very similar.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A substantially pure crystalline form A of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 7.9, 9.2, 12.5, 15.2, 18.4, 19.4, 19.7, 19.8, 27.7 and 28.7 (2θ degrees).

2. The substantially pure crystalline form of claim 1, wherein the x-ray powder diffraction pattern is as shown in FIG. 1.

3. A substantially pure crystalline form B of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 10.6, 12.1, 13.6, 14.1, 15.7, 16.9, 19.4, 20.3, 22.2, 23.4, 24.4, 24.8, 25.5 and 27.7 (2θ degrees).

4. The substantially pure crystalline form of claim 3, wherein the x-ray powder diffraction pattern is as shown in FIG. 1.

5. A substantially pure crystalline form C of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 8.5, 9.7, 11.6, 12.8, 13.6, 15.1, 16.1, 17.1, 18.2, 19.4, 20.4, 21.5, 22.9, 23.4, 24.5, 25.5, 29.9 and 30.5 (2θ degrees).

6. The substantially pure crystalline form of claim 5, wherein the x-ray powder diffraction pattern is as shown in FIG. 1.

7. A substantially pure crystalline form $H_A$ of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 7.7, 13.0, 13.4, 14.4, 16.7, 17.5, 17.8, 18.5, 19.8, 20.1, 21.7, 22.0, 22.3, 22.7, 23.3, 24.2, 24.4, 25.6, 27.0, 28.1 and 29.5 (2θ degrees).

8. The substantially pure crystalline form of claim 7, wherein the x-ray powder diffraction pattern is as shown in FIG. 1.

9. A substantially pure crystalline form $H_B$ of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 8.0, 9.5, 10.2, 14.3, 16.9, 17.7, 18.4, 18.7, 19.1, 19.4, 21.2, 21.4 and 27.4 (2θ degrees).

10. The substantially pure crystalline form of claim 9, wherein the x-ray powder diffraction pattern is as shown in FIG. 1.

11. A substantially pure crystalline form A of the maleate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 6.9, 8.9, 9.3, 10.3, 13.7, 16.8, 17.8, 19.6, 20.7, 24.7, 25.4 and 27.7 (2θ degrees).

12. The substantially pure crystalline form of claim 11, wherein the x-ray powder diffraction pattern is as shown in FIG. 2.

13. A substantially pure crystalline form $H_A$ of the maleate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 7.0, 8.5, 9.4, 11.0, 11.7, 12.4, 13.7, 23.1, 24.2, 24.9, 28.5 and 30.2 (2θ degrees).

14. The substantially pure crystalline form of claim 13, wherein the x-ray powder diffraction pattern is as shown in FIG. 2.

15. A substantially pure crystalline form A of the hemi-tartarate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 9.8, 11.9, 14.2, 15.8, 16.8, 20.2, 21.1, 21.7 and 25.0 (2θ degrees).

16. The substantially pure crystalline form of claim 15, wherein the x-ray powder diffraction pattern is as shown in FIG. 3.

17. A substantially pure crystalline form B of the hemi-tartarate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 9.7, 11.9, 13.7, 14.2, 15.8, 17.8, 18.8, 21.2, 21.7, 24.9, 25.9 and 27.9 (2θ degrees).

18. The substantially pure crystalline form of claim 17, wherein the x-ray powder diffraction pattern is as shown in FIG. 3.

19. A substantially pure crystalline form C of the hemi-tartarate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 10.2, 11.5, 13.3, 16.1, 16.9, 17.2 and 19.8 (2θ degrees).

20. The substantially pure crystalline form of claim 19, wherein the x-ray powder diffraction pattern is as shown in FIG. 3.

21. A substantially pure crystalline form A of the mesylate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 4.1, 8.2, 14.5, 18.1, 18.4, 19.8, 23.5 and 24.6 (2θ degrees).

22. The substantially pure crystalline form of claim 21, wherein the x-ray powder diffraction pattern is as shown in FIG. 4.

23. A substantially pure crystalline form B of the mesylate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 7.6, 11.5, 13.8, 15.1, 17.3, 18.9, 20.4, 21.7, 23.7 and 24.0 (2θ degrees).

24. The substantially pure crystalline form of claim 23, wherein the x-ray powder diffraction pattern is as shown in FIG. 4.

25. A substantially pure crystalline form of a salt of N-hydroxy-3-[4-[[[2-(2-methyl-1H-indol-3-yl)ethyl]amino]methyl]phenyl]-2E-2-propenamide selected from the group consisting of:
(a) form A of the acetate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.1, 8.2, 8.1, 12.6, 16.3, 21.8 and 23.2 (2θ degrees);
(b) form $S_A$ of the acetate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.9, 8.4, 9.0, 16.5, 20.3, 22.6, 23.4 and 24.4 (2θ degrees);
(c) form A of the benzoate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 6.6, 7.9, 13.2, 16.4, 16.8, 19.1, 23.6 and 24.1 (2θ degrees);
(d) form $S_A$ of the benzoate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 9.2, 9.6, 11.5, 12.6, 18.5, 19.4, 23.1 and 23.4 (2θ degrees);
(e) form $S_B$ of the benzoate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 9.3, 11.6, 12.2, 17.9, 21.0, 23.3, 24.1 and 24.6 (2θ degrees);
(f) form A of the hemi-fumarate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 11.5, 12.5, 15.8, 17.2, 18.8, 22.9, 24.5 and 25.0 (2θ degrees);
(g) form B of the hemi-fumarate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 11.6, 11.9, 12.5, 14.1, 15.8, 22.9, 24.2 and 27.9 (2θ degrees);
(h) form $H_A$ of the hemi-fumarate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.0, 10.1, 11.2, 15.1, 22.1 and 22.8 (2θ degrees);
(i) form A of the hemi-malate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 9.7, 12.0, 14.2, 15.9, 16.9, 20.3, 21.4 and 21.9 (2θ degrees);
(j) form $S_A$ of the hemi-malate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 6.6, 7.2, 9.4, 16.1, 18.4, 19.0, 21.9 and 22.4 (2θ degrees);
(k) form A of the phosphate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.3, 9.4, 16.7, 17.7, 18.4, 21.5, 24.3 and 26.9 (2θ degrees);
(l) form $S_A$ of the phosphate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 8.4, 16.5, 20.2, 21.8, 23.6, 25.4 and 31.0 (2θ degrees);
(m) form $S_B$ of the phosphate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 6.2, 7.5, 8.2, 17.9, 22.1, 22.6, 23.7 and 25.5 (2θ degrees);
(n) form $H_A$ of the phosphate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.4, 7.6, 8.3, 16.2, 17.4, 18.1 and 24.4 (2θ degrees);
(o) form A of the propionate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.0, 8.2, 9.5, 12.6, 14.1, 14.5, 18.4, 22.0, 23.9 and 25.5 (2θ degrees);
(p) form $S_A$ of the propionate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.0, 8.1, 8.7, 11.2, 12.0, 12.5, 16.1, 19.8 and 22.3 (2θ degrees);
(r) form A of the sulfate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 8.9, 10.2, 13.4, 16.1, 18.5, 22.0, 22.7 and 23.4 (2θ degrees);
(s) form $S_A$ of the sulfate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 4.6, 9.1, 13.7, 15.2, 18.4, 20.2, 22.5 and 22.9 (2θ degrees);
(t) form A of the hemi-succinate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 11.6, 12.5, 15.6, 17.3, 18.8, 23.1 and 24.7 (2θ degrees);
(u) form B of the hemi-succinate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.2, 7.7, 9.7, 11.5, 13.1, 15.1, 16.1 and 19.1 (2θ degrees);
(v) form $S_A$ of the hemi-succinate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.0, 10.2, 10.6, 11.1, 18.1 and 19.9 (2θ degrees); and
(w) form $H_A$ of the hemi-succinate salt of N-hydroxy-3-[4-[[[2-(2-methyl-1H-indol-3-yl)ethyl]amino]methyl]phenyl]-2E-2-propenamide characterized by an x-ray powder diffraction pattern having at least two maxima selected from 7.5, 11.6, 12.5, 14.1, 17.4, 23.0, 24.3 and 28.4 (2θ degrees).

26. The substantially pure crystalline form of claim 25, wherein the substantially pure crystalline form is selected from the group consisting of:
(a) form A of the acetate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 5;
(b) form $S_A$ of the acetate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 5;
(c) form A of the benzoate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 6;
(d) form $S_A$ of the benzoate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 6;
(e) form $S_B$ of the benzoate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 6;
(f) form A of the hemi-fumarate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 7;
(g) form B of the hemi-fumarate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 7;
(h) form $H_A$ of the hemi-fumarate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 7;
(i) form A of the hemi-malate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 8;
(j) form $S_A$ of the hemi-malate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 8;
(k) form A of the phosphate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 9;
(l) form $S_A$ of the phosphate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 9;
(m) form $S_B$ of the phosphate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 9;
(n) form $H_A$ of the phosphate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 9;
(o) form A of the propionate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 10;
(p) form $S_A$ of the propionate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 10;
(r) form A of the sulfate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 11;
(s) form $S_A$ of the sulfate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 11;
(t) form A of the hemi-succinate salt of N-hydroxy-3-[4-[[[2-(2-methyl-1H-indol-3-yl)ethyl]amino]methyl]

phenyl]-2E-2-propenamide, wherein the x-ray powder diffraction pattern is as shown in FIG. 12;

(u) form B of the hemi-succinate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 12;

(v) form $S_A$ of the hemi-succinate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 12; and (w) form $H_A$ of the hemi-succinate salt of N-hydroxy-3-[4-[[[2-(2-methyl-1H-indol-3-yl)ethyl]amino]methyl]phenyl]-2E-2-propenamide, wherein the x-ray powder diffraction pattern is as shown in FIG. 12.

27. A substantially pure crystalline form A of the DL-lactate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 9.9, 11.4, 13.8, 15.7, 18.2, 19.7, 20.3, 21.5, 25.3, 27.4 and 30.0 (2θ degrees).

28. A substantially pure crystalline form A of the DL-lactate salt of N-hydroxy-3-[4-[[[2-(2-methyl-1H-indol-3-yl)ethyl]amino]methyl]phenyl]-2E-2-propenamide, wherein the substantially pure crystalline form is characterized by the x-ray powder diffraction patter as shown in FIG. 13A.

29. A substantially pure crystalline form $H_A$ of the DL-lactate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 8, 8.5, 9.0, 11.7, 13.7, 14.5, 15.1, 17.1, 17.4, 17.7, 18.5, 20.5 and 21.2 (2θ degrees).

30. The substantially pure crystalline form of claim 29, wherein the x-ray powder diffraction patter is as shown in FIG. 13B.

31. A substantially pure crystalline form $S_A$ of the DL-lactate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 9.9, 17.2, 17.7, 18.1, 19.5, 20.5, 21.4, 21.7, 22.5, 23.6, 24.6 and 26.1 (2θ degrees).

32. The substantially pure crystalline form of claim 31, wherein the x-ray powder diffraction patter is as shown in FIG. 13C.

33. A substantially pure crystalline form A of the L-lactate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 9.9, 11.4, 13.8, 18.1, 18.5, 19.7, 20.2, 21.6, 25.2 and 29.9 (2θ degrees).

34. The substantially pure crystalline form of claim 33, wherein the x-ray powder diffraction patter is as shown in FIG. 13D.

35. A substantially pure crystalline form A of the D-lactate salt of N-hydroxy-3-[4-[[[2-(2-methyl-1H-indol-3-yl)ethyl]amino]methyl]phenyl]-2E-2-propenamide, wherein the substantially pure crystalline form is characterized by an x-ray powder diffraction pattern having at least two maxima selected from 9.9, 11.4, 13.8, 18.1, 18.5, 19.7, 20.2, 21.6 and 25.2 (2θ degrees).

36. A substantially pure crystalline form A of the D-lactate salt of N-hydroxy-3-[4-[[[2-(2-methyl-1H-indol-3-yl)ethyl]amino]methyl]phenyl]-2E-2-propenamide, wherein the substantially pure crystalline form is characterized the x-ray powder diffraction patter is as shown in FIG. 13E.

37. A pharmaceutical composition comprising:
  (a) a therapeutically effective amount of a substantially pure crystalline form of claim 27; and
  (b) at least one pharmaceutically acceptable carrier, diluent, vehicle or excipient.

38. A method of treating a disease comprising administering to a subject in need of such treatment a therapeutically effective amount of a substantially pure crystalline form of claim 27, wherein the disease is cutaneous t-cell lymphoma, acute myeloid leukemia, myelodysplastic syndrome or castration-resistant prostate cancer.

39. A pharmaceutical composition comprising:
  (a) a therapeutically effective amount of a substantially pure crystalline form of claim 33; and
  (b) at least one pharmaceutically acceptable carrier, diluent, vehicle or excipient.

40. A method of treating a disease comprising administering to a subject in need of such treatment a therapeutically effective amount of a substantially pure crystalline form of claim 33, wherein the disease is cutaneous t-cell lymphoma, acute myeloid leukemia, myelodysplastic syndrome or castration-resistant prostate cancer.

41. A pharmaceutical composition comprising:
  (a) a therapeutically effective amount of a substantially pure crystalline form of claim 35; and
  (b) at least one pharmaceutically acceptable carrier, diluent, vehicle or excipient.

42. A method of treating a disease comprising administering to a subject in need of such treatment a therapeutically effective amount of a substantially pure crystalline form of claim 35, wherein the disease is cutaneous t-cell lymphoma, acute myeloid leukemia, myelodysplastic syndrome or castration-resistant prostate cancer.

* * * * *